United States Patent [19]

Kristiansen et al.

[11] Patent Number: 6,046,214
[45] Date of Patent: Apr. 4, 2000

[54] HETEROCYCLIC COMPOUNDS

[75] Inventors: Marit Kristiansen, Søborg; Palle Jakobsen, Værløse; Jane Marie Lundbeck, Glostrup; Birgitte Søkilde, Værløse; Karsten Lundgren, Frederiksberg, all of Denmark

[73] Assignee: Novo Nordisk A/S, Bagsvaerd, Denmark

[21] Appl. No.: 09/186,400

[22] Filed: Nov. 4, 1998

Related U.S. Application Data

[63] Continuation of application No. PCT/DK98/00177, May 6, 1998
[60] Provisional application No. 60/045,722, May 6, 1997.

[30] Foreign Application Priority Data

May 6, 1997 [DK] Denmark .................................. 0526/97

[51] Int. Cl.[7] .......................... A01N 43/40; A01N 43/04; C07H 19/00; C07D 211/40; C07D 211/36
[52] U.S. Cl. ........................... 514/328; 514/43; 536/28.1; 546/219; 546/242
[58] Field of Search .................... 546/242, 219; 536/28.1; 514/315, 43, 328

[56] References Cited

U.S. PATENT DOCUMENTS 5,844,102 12/1998 Sierks et al. ............................ 536/17.2

FOREIGN PATENT DOCUMENTS 0 344 383 12/1989 European Pat. Off. .
WO 95/24391 9/1995 WIPO .

OTHER PUBLICATIONS

Ichikawa et al, Chemical Abstract vol. 123 No. 33550, "Foule Synthesis of Glucose Type 1–N–imino Sugars" 1995.

Ichikawa et al., (1998) J. Am. Chem. Soc. 120: 3007–3018.

Jespersen et al., (1994) Tetrahedron 50(47): 13449–13460.

Dong et al., (1996) Biochemistry 35:2788–2795.

Jespersen et al., (1994) Angew. Chem. 106(17):1858–1860.

*Primary Examiner*—Alan L. Rotman
*Assistant Examiner*—Raymond Covington
*Attorney, Agent, or Firm*—Steven T. Zelson; Carol E. Rozek

[57] ABSTRACT

Novel piperidine compounds are provided, and those compounds are useful in the treatment and/or prevention of diabetes, and especially non-insulin dependent diabetes (NIDDM or type 2 diabetes) including overnight or meal treatment and treatment or prevention of longterm complications, such as retinopathy, neuropathy, nephropathy, and micro- and macroangiopathy; treatment of hyperglycemia, hypercholesterolemia, hypertension, hyperinsulinemia, hyperlipidemia, atherosclerosis or myocardial ischemia.

34 Claims, No Drawings

HETEROCYCLIC COMPOUNDS

CROSS-REFERENCE TO RELATED APPLICATIONS

This application is a continuation of PCT/DK98/00177 filed May 6, 1998 and claims priority under 35 U.S.C. 119 of Danish application 0526/97 filed May 6, 1997, and U.S. Provisional application 60/045,722 filed May 6, 1997, the contents of which are fully incorporated herein by reference.

The present invention relates to novel compounds, the use of these compounds as medicament, the use of these medicaments in the treatment and/or prevention of diabetes, and especially non-insulin dependent diabetes (NIDDM or type 2 diabetes) including overnight or meal treatment and treatment or prevention of long-term complications, such as retinopathy, neuropathy, nephropathy, and micro- and macroangiopathy; treatment of hyperglycemia, hypercholesterolemia, hypertension, hyperinsulinemia, hyperlipidemia, atherosclerosis or myocardial ischemia, pharmaceutical compositions containing these compounds and methods of preparing the compounds.

Diabetes is characterized by an impaired glucose metabolism manifesting itself among other things by an elevated blood glucose level in the diabetic patients. Underlying defects lead to a classification of diabetes into two major groups: type 1 diabetes, or insulin demanding diabetes mellitus (IDDM), which arises when patients lack β-cells producing insulin in their pancreatic glands, and type 2 diabetes, or non-insulin dependent diabetes mellitus (NIDDM), which occurs in patients with an impaired β-cell function besides a range of other abnormalities.

Type 1 diabetic patients are currently treated with insulin, while the majority of type 2 diabetic patients are treated either with sulfonylureas that stimulate f-cell function or with agents that enhance the tissue sensitivity of the patients towards insulin or with insulin. Among the agents applied to enhance tissue sensitivity towards insulin metformin is a representative example.

Even though sulfonylureas are widely used in the treatment of NIDDM this therapy is, in most instances, not satisfactory. In a large number of NIDDM patients sulfonylureas do not suffice to normalize blood sugar levels and the patients are, therefore, at high risk for acquiring diabetic complications. Also, many patients gradually lose the ability to respond to treatment with sulfonylureas and are thus gradually forced into insulin treatment. This shift of patients from oral hypoglycaemic agents to insulin therapy is usually ascribed to exhaustion of the β-cells in NIDDM patients.

In normals as well as in diabetics, the liver produces glucose in order to avoid hypoglycaemia. This glucose production is derived either from the release of glucose from glycogen stores or from gluconeogenesis, which is a de novo intracellular synthesis of glucose. In type 2 diabetes, however, the regulation of hepatic glucose output is poorly controlled and is increased, and may be doubled after an overnight fast. Moreover, in these patients there exists a strong correlation between the increased fasting plasma glucose levels and the rate of hepatic glucose production (reviewed in R. A. De Fronzo: *Diabetes* 37 (1988), 667–687; A. Consoli: *Diabetes Care* 15 (1992), 430 –441; and J. E. Gerich: *Horm.Metab.Res*. 26 (1992), 18–21). Similarly, hepatic glucose production will be increased in type 1 diabetes, if the disease is not properly controlled by insulin treatment.

Since existing forms of therapy of diabetes does not lead to sufficient glycaemic control and therefore are unsatisfactory, there is a great demand for novel therapeutic approaches. Since the liver in diabetes is known to have an increased glucose production, compounds inhibiting this activity are highly desirable. Recently, patent applications on inhibitors of the liver specific enzyme, glucose-6-phosphatase, which is necessary for the release of glucose from the liver, have been filed, for example German Offenlegungsschrift Nos. 4,202,183 and 4,202,184 and Japanese patent application No. 4-58565. All these known compounds are benzene derivatives.

Substituted N-(indole-2-carbonyl)-glycinamides acting as glycogen phosporylase inhibitors are disclosed in PCT-publications No. WO96/39384 and WO96/39385.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in colour due to the presence of lipid deposits found principally within smooth-muscle cells and in macrophages of the intima layer of the arteries and aorta. Further, it is postulated that most of the cholesterol found within the fatty streaks, in turn, give rise to development of the "fibrous plaque", which consists of accumulated intimal smooth muscle sells laden with lipid and surrounded by extra-cellular lipid, collagen, elastin and proteoglycans. The cells plus matrix form a fibrous cap that covers a deeper deposit of cell debris and more extra cellular lipid. The lipid is primarily free and esterified cholesterol. The fibrous plaque forms slowly, and is likely in time to become calcified and necrotic, advancing to the "complicated lesion" which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particular high risk. Such independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition which occurs in the human population as a secondary symptom to various other disorders such as renal artery stenosis, pheochromocytoma or endocrine disorders. However, hypertension is also evidenced in many patients in whom the causative agent or disorder is unknown. While such "essential" hypertension is often associated with disorders such as obesity, diabetes and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure and stroke (brain hemorrhaging). These conditions are capable of causing short-term death in a patient. Hypertension can also contribute to the development of atherosclerosis and coronary disease. These conditions gradually weaken a patient and can lead to long-term death.

The exact cause of essential hypertension is unknown, though a number of factors are believed to contribute to the onset of the disease. Among such factors are stress, uncontrolled emotions, unregulated hormone release (the renin, angiotensin aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure and brain hemorrhaging. However, the development of atherosclerosis or heart disease due to hypertension over a long period of time remains a problem. This implies that although high blood pressure is being reduced, the underlying cause of essential hypertension is not responding to this treatment.

Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retension, among other things. These latter functions can be accomplished without affecting glucose levels and are known causes of hypertension. Peripheral vasculature growth, for example, can cause constriction of peripheral capillaires; while sodium retension increases blood volume. Thus, the lowering of insulin levels in hyperinsulinemics can prevent abnormal vascular growth and renal sodium retention caused by high insulin levels and thereby alleviate hypertension.

Cardiac hypertrophy is a significant risk factor in the development of sudden death, myocardial infarction, and congestive heart failure. Theses cardiac events are due, at least in part, to increased susceptibility of myocardial injury after ischemia and reperfusion which can occur in outpatient as well as perioperative settings. There is an unmet medical need to prevent or minimize adverse myocardial perioperative outcomes, particularly perioperative myocardinal infarction. Both non-cardiac and cardiac surgery are associated with substantial risks for myocardial infarction or death. Some 7 million patients undergoing non-cardiac surgery are considered to be at risk, with incidences of perioperative death and serious cardiac complications as high as 20–25% in some series. In addition, of the 400,000 patients undergoing coronary by-pass surgery annually, perioperative myocardial infarction is estimated to occur in 5% and death in 1–2%. There is currently no drug therapy in this area which reduces damage to cardiac tissue from perioperative myocardial ischemia or enhances cardiac resistance to ischemic episodes. Such a therapy is anticipated to be life-saving and reduce hospitalizations, enhance quality of life and reduce overall health care costs of high risk patients.

One object of the present invention is to provide compounds which can be used as medicaments for treatment of one or more of the above-mentioned diseases and disorders.

A further object of this invention is to provide compounds which can effectively be used in the treatment of diabetes, preferably type II diabetes, including overnight or meal treatment and preferably for treatment of increased plasma glucose levels.

A still further object of this invention is to provide compounds which can effectively be used as inhibitors of glucose production from the liver.

A still further object of this invention is to provide compounds which can be effectively used as phosphorylase inhibitors.

It has now been found that members of a novel group of piperidine compounds have interesting pharmacological properties. For example, the compounds of this invention can be used in the treatment of diabetes. Especially, the compounds of this invention are active as inhibitors of glucose production from the liver. Consequently, the compounds of this invention can be used for the treatment of the increased plasma glucose levels in diabetics.

Accordingly, it is an object of the invention to provide such novel piperidine compounds.

The compounds of the invention have the general formula I

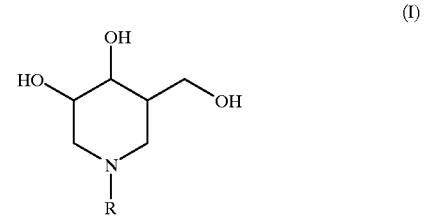

and pharmaceutically acceptable acid addition salts or hydrates or prodrugs hereof, wherein R is straight or branched $C_{1-6}$-alkoxy; or R is straight or branched ($C_{1-18}$-alkyl, $C_{2-18}$-alkene, or $C_{2-18}$-alkyne) all optionally substituted with cyano, carboxylic acid, trifluoromethyl, hydroxy, perhalomethyl, halogen, $C_{3-7}$-cycloalkyl, $C_{1-6}$-alkoxy, $C_{1-6}$-alkoxycarbonyl, benzyloxycarbonyl, or $NR_1R_2$ wherein $R_1$, $R_2$ both or one of them is hydrogen, $C_{1-6}$-alkyl, or benzyl; or R is straight or branched ($C_{1-18}$-alkyl, $C_{2-18}$-alkene, or $C_{2-18}$-alkyne) all optionally substituted with $SR_3$ wherein $R_3$ is $C_{1-6}$-alkyl, phenyl or carbonyl($C_{1-6}$-alkyl); or R is straight or branched ($C_{1-18}$-alkyl, $C_{2-18}$-alkene, or $C_{2-18}$-alkyne) all optionally substituted with carbonyl($C_{1-6}$)alkyl or carbonylphenyl optionally substituted with methoxy, nitro, halogen, or cyano; or R is straight or branched ($C_{1-18}$-alkyl, $C_{2-18}$-alkene, or $C_{2-18}$-alkyne) all optionally substituted with phenoxy or phenyl optionally substituted with trifluoromethyl, methoxy, $C_{1-6}$-alkyl, carboxylic acid, nitro, cyano, halogen, phenyl, methoxycarbonyl, methylsulfonyl; or R is straight or branched ($C_{1-18}$-alkyl, $C_{2-18}$-alkene, or $C_{2-18}$-alkyne) all optionally substituted with carboxamide ($CONR_4R_5$, wherein $R_4$, $R_5$ both or one of them is hydrogen or $C_{1-6}$-alkyl); or R is straight or branched ($C_{1-18}$-alkyl, $C_{2-18}$-alkene, or $C_{2-18}$-alkyne) all optionally substituted with naphthalene, phthalimide, optionally substituted piperidine, imidazoline, 2-thienone, optionally substituted coumarin, 2-dioxolane, hydantoin, thiohydantion, 1,2,4-oxadiazoline, optionally substituted isoxazolidine, tetrahydrofurfuryl, 1,4-benzodioxane, or phenylsulfonyl, or glycoside; or R is $C_{3-7}$-cycloalkyl optionally substituted with cyano, carboxylic acid, hydroxy, oxo, perhalomethyl, halogen, phenyl, $C_{1-6}$-alkoxy, $C_{1-6}$-alkoxycarbonyl, benzyloxycarbonyl, hydroxy-$C_{1-6}$-alkyl, or $NR_1R_2$ wherein $R_1$, $R_2$ both or one of them is hydrogen, $C_{1-6}$-alkyl, or benzyl.

The compounds of formula I may be presented as a mixture of enantiomers which, if desired, may be resolved into the individual pure enantiomers. This resolution may conveniently be performed by fractional crystallization from various solvents, of the salts of compounds of the formula I with optical active acids or by other methods known per se, for example, chiral column chromatography. This invention includes all isomers, whether resolved or mixtures thereof.

Examples of pharmaceutically acceptable salts are acid addition salts with non-toxic acids, either inorganic acids such as hydrochloric acid, hydrobromic acid, hydroiodic acid, sulphuric acid and phosphoric acid, or organic acids such as formic acid, acetic acid, trifluoroacetic acid, trichloroacetic acid, propionic acid, succinic acid, gluconic acid, lactic acid, citric acid, ascorbic acid, benzoic acid, embonic acid, methanesulphonic acid, ethanesulphonic acid, malonic acid, oxalic acid, maleic acid, pyruvic acid, tartaric acid, fumaric acid, mandelic acid, cinnamic acid, picric acid and the like acids, and include the pharmaceutically acceptable salts listed in Journal of Pharmaceutical Science, 66, 2 (1977) and incorporated herein by reference; pharmaceutically acceptable metal salts, such as lithium, sodium, potassium, or magnesium salts and the like. Also intended as pharmaceutically acceptable acid addition salts are the hydrates which the present compounds are able to form. The acid addition salts may be obtained as the direct products of compound synthesis. In the alternative, the free base may be dissolved in a suitable solvent containing the appropriate acid, and the salt isolated by evaporating the solvent or otherwise separating the salt and solvent. The compounds of this invention may form solvates with standard low molecular weight solvents using methods known to the skilled artisan.

In the above structural formula and throughout the present specification, the following terms have the indicated meaning:

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "$C_{3-7}$-cycloalkyl" as used herein refers to a radical of a saturated cyclic hydrocarbon with the indicated number of carbons such as cyclopropyl, cyclobutyl, cyclopentyl, cyclohexyl or cycloheptyl.

The term "halogen" means fluorine, chlorine, bromine or iodine.

The term "perhalomethyl" means trifluoromethyl, trichloromethyl, tribromomethyl or triiodomethyl.

The term "$C_{1-18}$-alkyl" as used herein, alone or in combination, refers to a straight or branched, saturated hydrocarbon chain having the indicated number of carbon atoms such as e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-hexyl, 1,2-dimethylpropyl, 2,2-dimethylpropyl, 1,2,2-trimethylpropyl and the like. The term "$C_{1-18}$-alkyl" as used herein also includes secondary $C_{3-18}$-alkyl and tertiary $C_{4-18}$-alkyl.

The term "prodrug" as used herein refers to e.g. to compounds of formula I that are drug precursors, which following administration, release the drug in vivo via some chemical or physiological process. Examples of such produgs are esters that upon cleavage release the corresponding free acid. Other examples of such prodrugs are compounds of formula I in which an ester group has been introduced and that upon cleavage release the corresponding free alcohol of formula I.

Certain of the above defined terms may occur more than once in the above formula I, and upon such occurrence each term shall be defined independently of the other.

In a preferred embodiment the invention relates to compounds of formula I, wherein R is straight or branched $C_{1-6}$-alkoxy.

In another preferred embodiment the invention relates to compounds of formula I, wherein R is straight or branched ($C_{1-18}$-alkyl, $C_{2-18}$-alkene, or $C_{2-18}$-alkyne) all optionally substituted with cyano, carboxylic acid, trifluoromethyl, hydroxy, perhalomethyl, halogen, $C_{3-7}$-cycloalkyl, $C_{1-6}$-alkoxy, $C_{1-6}$-alkoxycarbonyl, benzyloxycarbonyl, or $NR_1R_2$ wherein $R_1$, $R_2$ independently is hydrogen, $C_{1-6}$-alkyl, or benzyl.

In another preferred embodiment the invention relates to compounds of formula I, wherein R is straight or branched ($C_{1-18}$-alkyl, $C_{2-18}$-alkene, or $C_{2-18}$-alkyne) all optionally substituted with $SR_3$ wherein $R_3$ is $C_{1-6}$-alkyl, phenyl or carbonyl($C_{1-6}$-alkyl).

In another preferred embodiment the invention relates to compounds of formula I, wherein R is straight or branched ($C_{1-18}$-alkyl, $C_{2-18}$-alkene, or $C_{2-18}$-alkyne) all optionally substituted with carbonyl($C_{1-6}$)alkyl or carbonylphenyl optionally substituted with methoxy, nitro, halogen, or cyano.

In another preferred embodiment the invention relates to compounds of formula I, wherein R is straight or branched ($C_{1-18}$-alkyl, $C_{2-18}$-alkene, or $C_{2-18}$-alkyne) all optionally substituted with phenoxy or phenyl optionally substituted with trifluoromethyl, methoxy, $C_{1-6}$-alkyl, carboxylic acid, nitro, cyano, halogen, phenyl, methoxycarbonyl, methylsulfonyl.

In another preferred embodiment the invention relates to compounds of formula I, wherein R is straight or branched ($C_{1-18}$-alkyl, $C_{2-18}$-alkene, or $C_{2-18}$-alkyne) all optionally substituted with carboxamide ($CONR_4R_5$, wherein $R_4$, $R_5$ both or one of them is hydrogen or $C_{1-6}$-alkyl).

In another preferred embodiment the invention relates to compounds of formula I, wherein R is straight or branched ($C_{1-18}$-alkyl, $C_{2-18}$-alkene, or $C_{2-18}$-alkyne) all optionally substituted with naphthalene, phthalimide, optionally substituted piperidine, imidazoline, 2-thienone, optionally substituted coumarin, 2-dioxolane, hydantoin, thiohydantion, 1,2,4-oxadiazoline, optionally substituted isoxazolidine, tetrahydrofurfuryl, 1,4-benzodioxane, or phenylsulfonyl, or glycoside.

In another preferred embodiment the invention relates to compounds of formula I, wherein R is $C_{3-7}$-cycloalkyl optionally substituted with cyano, carboxylic acid, hydroxy, oxo, perhalomethyl, halogen, phenyl, $C_{1-6}$-alkoxy, $C_{1-6}$-alkoxycarbonyl, benzyloxycarbonyl, hydroxy-$C_{1-6}$-alkyl, $C_{1-6}$-alkyl or $NR_1R_2$ wherein $R_1$, $R_2$ both or one of them is hydrogen, $C_{1-6}$-alkyl, or benzyl.

The present invention also relates to the use of the novel compounds of the formula I as disclosed herein for the preparation of a medicament, especially for the preparation of a medicament for the treatment and/or prevention of hyperglycaemia or diabetes mellitus, preferably NIDDM.

The compounds of the present invention reduce elevated plasma glucose levels, and hence make them useful in the treatment and prevention of various diseases of the endocrinological system, especially ailments related to carbohydrate metabolism and especially the glucose metabolism, e.g. hyperglycaemia, diabetes mellitus, and especially non-insulin dependent diabetes mellitus (NIDDM) including long-term complications, such as retinopathy, neuropathy, nephropathy, and micro- and macroangiopathy. Moreover, the present compounds are useful in the prophylactic treatment of hyperlipidaemia, hypertension, liver and bile diseases, and atherosclerosis associated with diabetes. The present compounds are especially useful in the treatment of diseases associated with the activity of the liver enzyme glycogen phosphorylase, due to their capability of inhibiting said enzymatic activity.

Accordingly, in another aspect the invention relates to a compound of the general formula I, or a pharmaceutically acceptable acid addition salts or hydrates or prodrugs thereof for use as a therapeutically active substance, preferably for use as a therapeutically active substance in the treatment or prevention of diseases of the endocrinological system, preferably hyperglycaemia or diabetes.

Furthermore, the invention also relates to the use of the inventive compounds of formula I for the preparation of medicaments useful for treating or preventing hyperglycaemia or diabetes.

Moreover, the invention relates to a method of treating or preventing diseases of the endocrinological system, preferably diabetes, in a subject in need thereof comprising administering an effective amount of a compound according to the invention.

The compounds of invention may be prepared by a variety of synthetic routes, which include the methods described below:

a) Reacting a compound of formula (II)

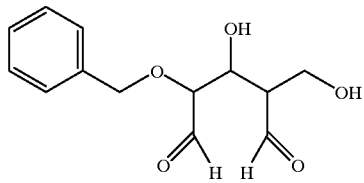

(II)

with NH$_2$R wherein R is as defined above to form a compound of the general formula (III):

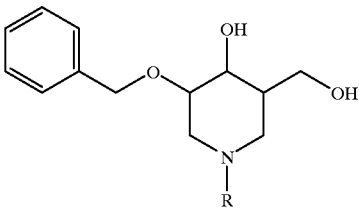

(III)

wherein R has the meanings set forth above, followed by debenzylation of a compound of formula (III) by catalytic reduction to form a compound of the general formula (I); or b) Reacting a compound of formula (III) wherein R is hydrogen with RX, wherein R has the meaning set forth above and X is a leaving group, e.g. halogen followed by debenzylation by catalytic reduction, to form a compound of the general formula (I); or c) Reacting a compound of formula (III) wherein R is hydrogen with RCHO, wherein R has the meaning set forth above, in presents of a reducing agent, e.g. sodium cyanoborohydride, followed by debenzylation by catalytic reduction, to form a compound of the general formula (I); or d) Reacting a compound of the formula (IV)

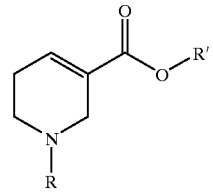

(IV)

wherein R has the meanings set forth above and R' is H or C$_{1-4}$-alkyl with an agent causing formation of a sodium or lithium salt of (IV) followed by quenching with acid, to form a compound of the general formula (V) using methods described in the literature (e.g. Aust. J. Chem. 36, (1983), 601–608).

An example of an salt formation agent is LDA and examples of quenching media are hydrochloric acid and ammonium chloride.

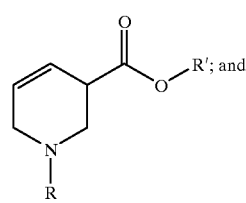

(V)

e) Reacting a compound of the formula (V) with a reducing agent such as lithium aluminium hydride, borane or similar hydrides to form a compound of the general formula (VI), wherein R has the meaning set forth above.

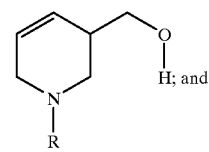

(VI)

f) Reacting a compound of the general formula (VI) with agents such tert-butyl hydroperoxide, trifluoroperacetic acid, metachloroperbenzoic acid, hydrogen peroxide or similar agents to introduce epoxide formation forming a compound of the general formula (VII) wherein R has the meaning set forth above.

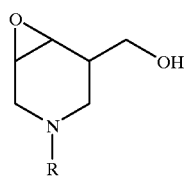

(VII)

This reaction can be carried out with unprotected hydroxymethyl group using the Sharpless epoxidation technique in which complexing agents as titanium compounds and tartrates are used to increase stereoselectivity (e.g. J. Org. Chem. 49 (1984) 3707–3711), or with the hydroxy-group protected with known OH protection groups (Greene and Wuts, Protective groups in organic synthesis, Wiley and sons, INC, 1990). The reaction advantageously be carried out on the salt (e.g. trifluoroacetate) of (VI) to avoid N-oxide formation.(e.g.Monatsh. Chemie 117 (1986) 859–865); and g) Reacting a compound of the general formula (VII) with agents causing epoxy ring opening, e.g. potassium hydroxide, forming a compound of the general formula (I), wherein R has the meaning set forth above; or h) Reacting a compound of the general formula (IV) in which R is an alkyl group and R' is H or $C_{1-4}$-alkyl with an dealkylating agent like 1-chloroethyl chloroformate, 3,3,3-tricholoroethyl chloroformate, phenyl chlorofor-mate or similar agents to cause N-dealkylation forming a compound of the general formula (VII) wherein R' has the meaning set forth above (J. Org. Chem. 49, (1984), 2081–2082; Aust. J. Chem. 36, (1983) 601–608).

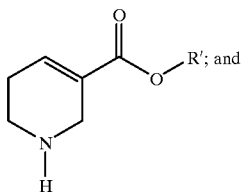

(VIII)

i) Reacting a compound of the general formula (VII) with an agent causing N-protection using methods known in the art (Greene and Wuts , Protective groups in organic chemistry, Wiley and sons, INC 1990) forming a compound of the general formula (IX), wherein Pg is an easily removable N-protection group and R' has the meaning set forth above.

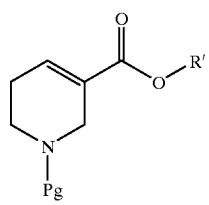

(IX)

Examples of easily removable N-protection groups are the Boc group or the CBZ group; and j) Reacting a compound of the general formula (IX) using the reaction sequence d)–e)–f)–g) followed by deprotection of the N-atom leading to a compound of the formula (I) in which R is hydrogen; or k) Reacting a compound of the general formula (X)

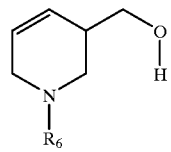

(X)

wherein $R_6$ can be R as defined above or a protecting group Pg as described above with a compound able to protect the hydroxymethyl group, e.g. acetyl chloride or similar acylating agents, forming a compound of the general formula (XI).

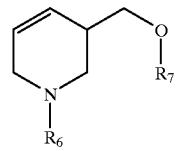

(XI)

wherein $R_6$ has the meaning as set forth above and $R_7$ being an acyl residue like acetyl, $C_{2-18}$-alkyl-carbonyl, menthyloxyacetyl, camphanoyl, α-methoxy-α-(trifluoromethyl)phenylacetyl or similar structures, either as separate enantiomers or as racemic mixtures. Preferably the acetylating agent could be a derivatives of an optical active carboxylic acid like R-(+)-α-methoxy-α-(trifluoromethyl) phenyl acetic acid, (−)-menthyloxy acetic acid, (−)-camphanic acid or the optical antipodes of such acid derivatives; and l) Reacting a compound of the general formula (XI) using the reaction sequence f)–g) followed by deprotection of N and O protection groups to form a compound of the general formula (I) wherein R either has the meaning set forth above or hydrogen; or m) Reacting a compound of formula (I) wherein R is hydrogen with a compound of the general formula (XII), wherein Su is a substrate and L is a linker:

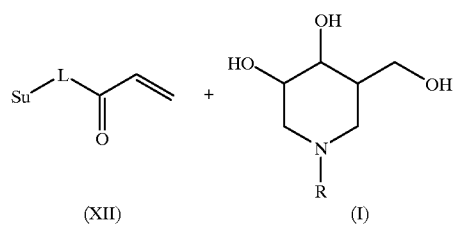

(XII)   (I)

to form a compound of the general formula (XIII):

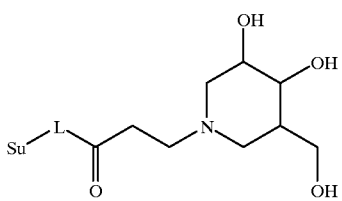

(XIV)

The substrate may be any insoluble or partially insoluble material, to which compounds may be covalently attached. Substrates may be selected from the group consisting of any kind of organic or inorganic poylmeric or oligomeric compound. Preferably the substrate may be selected from the groups consisting of polystyrene, polyethylene glycol (PEG), polyethylene glycol attached to poylstyrene, polyacrylamides, polyamides, polysaccharides and silicates. Depending on the type of substrate chosen, different types of solvents or protecting groups may be used.

The linker L is a molecule with at least two reactive sites, which permit its covalent attachment to other molecules or to a substrate. Either the bond of the linker to the substrate or the bond of the linker to other molecules attached to it or the linker itself must be cleavable upon selective exposure to an activator such as a selected chemical activator or other specific conditions, e.g. by treatment with a strong acid or by exposure to electromagnetic radiation or by metal catalysis; and n) Reacting a compound of the general formula (XIV) wherein Su and L have the meaning set forth above with RX, wherein R has set the meaning set forth above and X is a leaving group, e.g. halogen to form a compound of the general formula (XV):

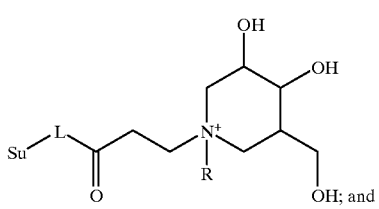

(XV)

o) Reacting a compound of the general formula (XV), wherein R, Su and L have the meaning set forth above with a cleaving agent, e.g. a strong base to form a compound of the general formula (I), wherein R has the meaning set forth above.

The starting materials employed in the synthesis of the compounds from formula II and IV are either known or may be prepared in conventional manner from commercially available materials, e.g according to the methods described in the examples.

The compounds of the invention have one or more asymmetric centres and it is intended that stereoisomers (optical isomers), as separated, pure, or partially purified stereoisomers or racemic mixtures thereof are included in the scope of the invention.

Preferred compounds of the invention are:
(3R,4R,5R)-1-Butyl-5-hydroxymethyl-3,4-piperidinediol,
(3R,4R,5R)-1-(3-Cyclohexyl)propyl)-3,4-dihydroxy-5-hydroxymethylpiperidin,
(3R,4R,5R)-1-Dodecyl-5-hydroxymethyl-3,4-piperidinediol,
(3R,4R,5R)-1-(2-Hydroxyethyl)-5-hydroxymethyl-3,4-piperidinediol,
(3R,4R,5R)-5-Hydroxymethyl-1-(4-(5-hydantoyl)butyl)-3,4-piperidinediol,
(3R,4R,5R)-5-Hydroxymethyl-1-(3-phenylpropyl)-piperidine-3,4-diol,
(3R,4R,5R)-5-hydroxymethyl-1-methyl-3,4-piperidinediol,
(3R,4R,5R)-5-Hydroxymethyl-1-methoxy-3,4-piperidinediol,
(3R,4R,5R)-5-Hydroxymethyl-1-(4-N,N-diphenylaminobenzyl)-3,4-piperidinediol,
(3R,4R,5R)-1-Acetyl-5-hydroxymethyl-3,4-piperidinediol,
(3R,4R,5R)-5-Hydroxymethyl-1-(3-phenylallyl)-3,4-piperidinediol,
(3R,4R,5R)-1-Allyl-5-hydroxymethyl-3,4-piperidinediol,
(3R,4R,5R)-1-Benzyl-5-hydroxymethyl-3,4-piperidinediol,
(3R,4R,5R)-1-Octyl-5-hydroxymethyl-3,4-piperidinediol,
(3R,4R,5R)-2-(3,4-Dihydroxy-5-hydroxymethyl-piperidin-1-yl)-acetamide,
Ethyl ((3R,4R,5R)-3,4-dihydroxy-5-hydroxymethyl-piperidin-1-yl)acetate,
(3R,4R,5R)-5-Hydroxymethyl-1-(4-trifluoromethyl-benzyl)-3,4-piperidinediol,
(3R,4R,5R)-1-(2-(4'-Fluoroacetophenone))-5-hydroxymethyl-3,4-piperidinediol,
(3R,4R,5R)-5-Hydroxymethyl-1-(2-(4'-methoxyacetophenone))-3,4-piperidinediol,
(3R,4R,5R)-(2-(4-Fluorophenoxy)-ethyl)-5-hydroxymethyl-3,4-piperidinediol,
(3R,4R,5R)-5-Hydroxymethyl-1-(4-phenoxy-butyl)-3,4-piperidinediol,
(3R,4R,5R)-1-(4-Cyanobutyl)-5-hydroxymethyl-3,4-piperidinediol,
(3R,4R,5R)-1-(10-Decylphthalimido)-5-hydroxymethyl-3,4-piperidinediol,
(3R,4R,5R)-12-(3,4-Dihydroxy-5-hydroxymethyl-piperidin-1-yl)-dodecanoic acid,
(3R,4R,5R)-5-Hydroxymethyl-1-phenoxyethyl-3,4-piperidinediol,
($^3$R,$^4$R,5R)-3-(3,4-Dihydroxy-5-hydroxymethyl-piperidin-1-yl)propionic acid
(3R,4R,5R)-1-(6-Deoxy-1-O-methyl-6-α-D-glucopyranosyl)-5-hydroxymethyl-3,4-piperidinediol
or pharmaceutically acceptable salts or hydrates or prodrugs thereof as defined herein, or any optical isomer or mixture of optical isomers, including a racemic mixture, or any tautomeric form.

Other compounds of the general formula I can be prepared by the above strategy. A variety of functional groups can be introduced in the compounds prepared as outlined above by methods well known to those skilled in the art.

Pharmaceutical Compositions

This invention further provides pharmaceutical compositions which comprise at least one compound of formula I or a pharmaceutically acceptable salt thereof in connection with a pharmaceutically acceptable carrier. Such compositions may be in the form of powders, solutions, or suspensions, which may or may not be divided in unit dosage form or in the form of capsules or tablets. Liquid compositions include sterile solutions, suspensions and emulsions suitable for parenteral injection.

The pharmaceutical compositions of this invention may comprise carriers, diluents, absorption enhancers, tablet disintegrating agents and other ingredients which are conventionally used in the art. The powders and tablets preferably contain from 5 to 99%, more preferred from 10 to 90% of the active ingredient. Examples of solid carriers are magnesium carbonate, magnesium stearate, cyclodextrin, dextrin, lactose, sugar, talc, gelatine, pectin, tragacanth, methyl cellulose, sodium carboxymethyl cellulose, low melting waxes and cocoa butter.

The route of administration of the compositions containing a compound of formula I may be any route which effectively transports the active compound to its site of action, the oral or nasal route being preferred.

If a solid carrier is used for oral administration the preparation may be tabletted, placed in a hard gelatin capsule in powder or pellet form, or it can be in the form of a troche or lozenge. If a liquid carrier is used the preparation may be in the form of a syrup, emulsion, soft gelatin capsule or sterile injectable liquid such as an aqueous or non-aqueous liquid suspension or solution. Tablets, dragees, or capsules having talc and/or a carbohydrate carrier or binder or the like are particularly suitable for oral application. Preferable carriers for tablets, dragees, and capsules include lactose, corn starch, and/or potato starch.

For parenteral application particularly suitable are injectable solutions or suspensions, preferably aqueous solutons with the active compound dissolved in polyhydroxylated castor oil.

A typical tablet which may be prepared by conventional tabletting techniques may contain:

| Core: | |
|---|---|
| Active compound (as free compound or salt thereof) | 50 mg |
| Collioidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

The compounds of the invention may be administered to a mammal, especially a human in need of such treatment, prevention, elimination, alleviation or amelioration of the various diseases as mentioned above and especially diabetes. Such mammals include also animals, both domestic animals, e.g. household pets, and non-domestic animals such as wildlife.

The regimen for any patient to be treated with the compositions according to the present invention should be determined by those skilled in the art. The daily dose to be administered in therapy can be determined by a physician and will depend on the particular compound employed, on the route of administration and on the age and the condition of the patient. A convenient daily dosage can be less than about 1 g, preferably in the range around 10–200 mg.

Experimental Protocol and Results

For in vivo studies, female ob/ob mice (20 g) fasted for 3 hours were used. Test compounds or NaCl (0.9%; controls) were administered intraveneously (hereinafter designated i.v.). Blood samples were drawn from the orbital vein and analyzed for glucose using a glucose oxidase method.

Rat hepatocytes were isolated using a standard two step collagenase technique, and cultured onto collagen coated culture dishes for 72 hours in medium 199 with the addition of dexamethazone (0.1 mM); penicillin/Streptomycin ((100 u/100 mg)/ml) and insulin (1 nM). During the last 24 hours, the hepatocytes were cultured in the presence of high levels of insulin (5 nM) and glucose (15 mM), which result in the incorporation of glucose into glycogen. Therefore, at the time of the experiment, the cells mimic livers from fed animals.

Experiments were initiated after 48 hours of culture by 2 times wash of cells and addition of a 20 mM HEPES experimental buffer including balanced salts, but without glucose. The test compound was added simultaneously with the experimental buffer. To some cultures, glucagon (0.5 nM) was added after 10 minutes in order to stimulate glucose production from liver cells. The glucose released into the media, reflecting the glucose production of the liver cells, was measured 70 minutes after the start of the experiment and standardized to cellular DNA content.

Phosphorylase was either purchased from Sigma or extracted from rat livers according to Stalmans et. al. (Eur.J.Biochem. 49 (1974), 415). The activity of phosphorylase was determined as described by Bergmeyer (1983; in: Meth. of Enzymatic Analysis, 2, 293–295, Weinheim, (ed.) Verlag Chemie).

Compounds of the invention shows their effect in lowering the glucagon mediated increase in plasma glucose.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLE 1

(3R,4R,5R)-3-Benzyloxy-1-butyl-5-hydroxymethyl-4-piperidinol (3R,4R,5R)-3-Benzyloxy-5-hydroxymethyl-4-piperidinol (87 mg, 0.37 mmol), 1-iodobutane (81 mg, 0.44 mmol, 50 μl), potassium carbonate (154 mg, 1.1 mmol) and dry acetone (8 ml) were stirred for 24h at 40° C. under a nitrogen atmosphere. The solvent was evaporated in vacuo, and the residue purified on a silica gel column (Eluent: ethyl acetate/methanol/25% ammonium hydroxide (6/1/1%)). This afforded the free base of (3R,4R,5R)-3-benzyloxy-1-butyl-5-hydroxymethyl-4-piperidinol (Yield: 72 mg, 67%).

$^1$H-NMR(CD$_3$OD) in ppm: δ7,4–7,2 (m, 5H); 4,70 (dd, 2H); 3,80 (dd, 1H); 3,54 (m,1H);3,34 (m, 1H); 3,25 (d, 1H); 3,08 (m, 2H); 2,38 (t, 2H); 1,85 (dd, 2H); 1,70 (m, 1H); 1,45 (m,2H); 1,31 (m, 2H); 0,93 (t, 3H).

In a similar way the following compounds were prepared:

(3R,4R,5R)-3-Benzyloxy-1-dodecyl-5-hydroxymethylpiperidin-4-ol from (3R,4R,5R)-3-benzyloxy-5-hydroxymethyl4-piperidinol and iodododecane.

$^1$H-NMR(CD$_3$OD) in ppm: δ7,4–7,2 (m, 5H); 4,70 (dd, 2H); 3,80 (dd, 1H); 3,54 (m, 1H);3,34 (m, 1H); 3,25 (d, 1H); 3,08 (m, 2H); 2,38 (t, 2H); 1,89 (dd, 2H); 1,78 (m, 1H); 1,5 (m,2H); 1,3 (m, 18H); 0,9 (t, 3H).

(3R,4R,5R)-3-Benzyloxy-1-(2-hydroxyethyl)-5-hydroxymethyl-4-piperidinol from (3R,4R, 5R)3-benzyloxy-5-hydroxymethyl-4-piperidinol and 2-bromoethanol with catalytic amounts of potassium iodide.

$^1$H-NMR (CD$_3$OD+10% d$_6$-benzene) in ppm: δ1.9 (m,1H), 2.2 (ddd, H), 2.7 (t, 2H) 3,1–3.65 (m, 5H), 3.7 (t, 2H), 3.87 (dd, 1H), 4.7 (dd, 2H), 4.9 (s, 3H), 7.2–7.5 (m,5H). $^{13}$C-NMR (CD$_3$OD) in ppm: δ43.61, 55.18, 55.93, 58.25, 59.68, 61.19, 63.33, 72.75, 73.20, 79.29, 127.76, 128.10, 128.39, 138.99. MS (FAB): m/e 281 (M$^+$).

(3R,4R,5R)-5-Benzyloxymethyl-1-(4-(5-hydantoyl)butyl)-3,4-piperidinediol from (3R,4R,5R) 3-benzyloxy-5-hydroxymethyl-4-piperidinol and 5-(4-chlorobutyl)hydantoin with catalytic amounts of potassium iodide.

$^1$H-NMR(CD$_3$OD) in ppm: δ7,4–7,2 (m, 5H); 4,70 (d, 2H); 4,1 (m, 1H); 3,8 (dd, 1H); 3,6–3.0 (m, 6H); 2,4 (m, 2H),1,3–0,9 (m, 8H).

(3R,4R,5R)-3-Benzyloxy-5-hydroxymethyl-1-(3-phenyl-propyl)-piperidin4-ol from (3R,4R,5R)-3-benzyloxy-5-hydroxymethyl-4-piperidinol and 3-bromo-1-phenylpropane with catalytic amounts of potassium iodide.

$^1$H-NMR(CD$_3$OD) in ppm: δ7,4–7,1 (m, 10H); 4,70 (dd, 2H); 3,80 (dd, 1H); 3,50 (m,1H); 3,40 (m, 1H); 3,25 (t, 1H); 3,01 (m, 2H); 2,53, (t, 2H); 2,33 (m, 2H); 1,75 (m, 5H).

EXAMPLE 2

(3R,4R,5R)-3-Benzyloxy-1-(3-(cyclohexyl)propyl)-5-hydroxymethylpiperidin-4-ol (3R,4R,5R)-3-Benzyloxy-5-hydroxymethyl-4-piperidinol (0.397 g, 1.7 mmol) was dissolved in dry methanol (5ml) and HCl$_g$ in methanol (2N) was added in excess. Evaporation to dryness in vacuo afforded the hydrochloride salt. The salt was dissolved in dry methanol (20ml) and sodium cyanoborohydride (0.126 g, 2.0 mmol) was added. HCl$_g$ in methanol (2N) was added dropwise to obtain pH=6 of the mixture (2 dr). Cyclohexylpropionaldehyde (0.306 ml, 0.281 g, 2.0 mmol) was added, and the mixture was stirred under a nitrogen atmosphere for 18h at room temperature. HCl$_g$ in methanol (2N) was added a couple of times to maintain pH=6 of the solution. Concentration in vacuo and purification of the residue on a silica gel column (Eluent: ethyl acetate/methanol/25% ammonium hydroxide (6/1/1%)) afforded (3R,4R,5R)-3-benzyloxy-1-(3-(cyclohexyl)propyl)-5-hydroxymethylpiperidin4-ol (Yield: 0.58 g, 96%.

$^1$H-NMR (CDCl$_3$) in ppm: δ7,4–7,2 (m, 5H); 4,62 (dd, 2H); 3,68 (m, 3H); 3,52–3,35 (m, 2H); 3,16 (m, 1H); 2,82 (m, 1H); 2,32 (t, 2H); 1,90 (m, 1H); 1,87–1,59 (m, 5H); 1,44 (m,2H); 1,15 (m, 7H); 0,88 (m, 2H).

EXAMPLE 3

(3R,4R,5R)-1-Benzyl-3-benzyloxy-5-hydroxymethylpiperidin4-ol

4-O-Benzyl-2-deoxy-2-C-hydroxymethyl-D-glucopyranose (6.0 g, 21.1 mmol) (preparation see WO 95/24391) was dissolved in methanol (200 ml). Sodium periodate (21.4 g, 100 mmol) in water (200 ml) was added dropwise over 15 min. The mixture was stirred at 45–47° C. for 3.5 h. The precipitate was filtered off and the mixture was concentrated and purified by flash chromatography on silica gel using ethyl acetate as eluent. The purified product of 4-O-benzyl-2-deoxy-2-C-hydroxymethyl-D-xylo-pentodialdose was dissolved in methanol (50 ml) and benzyl amine (4.36 g, 40.7 mmol) and sodium cyanoborohydride (1.0 g, 15.9 mmol) was added. The mixture was stirred at room temperature for 3 days. Subsequently the mixture was acidified to pH=2 with conc. hydrochloric acid and evaporated to dryness. The residue was dissolved in water ( 50 ml), pH was adjusted to 10 with aqueous sodium hydroxide and the solution was extracted with methylene chloride. The organic phase was dried over magnesium sulphate, evaporated and purified on silica gel using ethyl acetate as eluent. This afforded (3R,4R,5R)-1-benzyl-3-benzyloxy-5-hydroxymethylpiperidin-4-ol as an oil (Yield: 25%).

$^1$H-NMR (CDCl$_3$) in ppm: d 1.6–1.85 (m, 3H), 2.8–3.5 (m, 7H), 3.7 (dd, 1H), 4.55 (dd, 2H), 4.8 (s, 2H), 7.1–7.3 (m. 10H)

$^{13}$C-NMR (CDCl$_3$) in ppm: d 44.07, 55.02, 55.92, 61.65, 62.46, 72.43, 74.05, 80.20, 127.14, 127.33, 127.549, 128.54, 128.22, 128.27, 129.42, 137.48, 139.01, 172.84

In a similar way the following compounds were prepared:

(3R,4R,5R)-3-Benzyloxy-5-hydroxymethyl-1-methyl-piperidin-4-ol from 4-O-benzyl-2-deoxy-2-C-hydroxymethyl-D-xylo-pentodialdose prepared as described above (2.78 g), methyl amine hydrochloride (1.16 g) and sodium cyanoborohydride (0.62 g) in methanol (50 ml).

$^1$H-NMR (CDCl$_3$) in ppm: d 1.8 (ddd, 2H), 1.9 (m, 1H), 2.3 (s, 1H), 2.75 (m, 1H), 3.1 (m, 1H), 3.2–3.8 (m, 6H), 4.6 (dd, 2H), 7.2–7.4 (m, 5H); $^{13}$C-NMR ( CDCl$_3$) in ppm: d 42.07, 44.97, 55.59, 56.75, 63.11, 71.27, 75.06, 79.12, 126.94, 127.01, 127.65, 137.38.

(3R,4R,5R,)-3-Benzyloxy-5-hydroxymethyl-1-methoxy-4-piperidinol from 4-O-benzyl-2-deoxy-2-C-hydroxymethyl-D-xylo-pentodialdose prepared as described above (0.8 g), met-hoxyamine hydrochloride (0.54 g) and sodium cyanoborohydride (0.18 g) in methanol (50 ml). MS(SP): m/e 267 (M$^+$).

EXAMPLE 4

(3R,4R,5R)-1-Butyl-5-hydroxymethyl-3,4-piperidinediol (Compound 1)

(3R,4R,5R)-3-Benzyloxy-1-(n-butyl)-5-hydroxymethyl-4-piperidinol (105 mg, 0.4 mmol) was dissolved in ethanol (20ml) containing aqueous hydrochloric acid (4N, 0.3 ml), and palladium on carbon (10%, 30mg) was added. The mixture was hydrogenated at 1 atm. H$_2$-pressure for 3h, filtered through celite and concentrated in vacuo. Purification on a silica gel column (Eluent: ethyl acetate/methanol/25% ammonium hydroxide (4/1/1%)) gave the free base of (3R,4R,5R)-1-butyl-5-hydroxymethyl-3,4-piperidinediol (Yield: 53 mg, 74%) as a semicrystalline compound.

M.p. 94–95° C. MS(SP): m/e 203 (M$^+$). $^1$H-NMR (CD$_3$OD) in ppm: d 3,80 (dd, 1H); 3,51 (m2H); 3,06 (m, 3H); 2,43 (dd, 2H); 1,91 (dt, 2H); 1,75 (m, 1H); 1,53 (m, 2H); 1,33 (m, 2H); 0,92 (t, 3H).

In a similar way the following compounds were prepared:

(3R,4R,5R)-1-(3-Cyclohexyl)propyl)-3,4-dihydroxy-5-hydroxymethylpiperidin (Compound 2) from (3R,4R,5R)-3-benzyloxy-1-(3-(cyclohexyl)propyl)-5-hydroxymethylpiperidin-4-ol.

M.p. 107–108° C. MS(FAB): m/z 272 (M+1). $^1$H-NMR (CD$_3$OD) in ppm: d 3,80 (dd, 1H); 3,50 (m 2H); 3,06 (m, 3H); 2,37 (m, 2H); 1,88–1,58 (m, 8H);1,52 (m, 2H); 1,2 (m, 6H); 0,90 (m, 2H).

(3R,4R,5R)-1-Dodecyl-5-hydroxymethyl-3,4-piperidinediol (Compound 3) from (3R,4R,5R)3-benzyloxy-1-dodecyl-5-hydroxymethyl-4-piperidinol.

M.p. 59–60° C. MS(SP): m/e 315 (M$^+$). $^1$H-NMR (CD$_3$OD) in ppm: d 3,80 (dd, 1H); 3,51 (m, 2H); 3,06 (m, 3H); 2,40 (dd, 2H); 1,91 (dt, 2H); 1,75 (m, 1H); 1,53 (m, 2H); 1,3 (m, 20H); 0,9 (t, 3H).

(3R,4R,5R)-1-(2-Hydroxyethyl)-5-hydroxymethyl-3,4-piperidinediol (Compound 4) from (3R,4R,5R)-3-benzyloxy-1-(2-hydroxyethyl)-5-hydroxymethyl-4-piperidinol.

MS(SP): m/e 191 (M$^+$).

(3R,4R,5R)-5-Hydroxymethyl-1-(4-(5-hydantoyl)buiyl)-3,4-piperidinediol (Compound 5) from (3R,4R,5R)-5-benzyloxymethyl-1-(4-(5-hydantoyl)butyl)-3,4-piperidinediol.

¹H-NMR (CD₃OD) in ppm: d 4.1 (m, 1H), 3.8 (dd,1H), 3.6–3.1 (m, 6H), 2.55 (m, 2H); 2.1–1.4 (m, 8H).

(3R,4R,5R)-5-Hydroxymethyl-1-(3-phenylpropyl)-piperidine-3,4-diol (Compound 6) from (3R,4R,5R)-3-benzyloxy-5-hydroxymethyl-1-(3-phenylpropyl)-piperidin-4-ol.

¹H-NMR (CD₃OD) in ppm: d 7,2 (m, 5H); 3,80 (dd, 1H); 3,50 (m, 2H); 3,06 (m, 3H); 2,62 (t, 2H); 2,40 (m, 2H); 1,92–1,70 (m, 3H); 1,23 (m, 2H).

(3R,4R,5R)-5-Hydroxymethyl-1-methyl-3,4-piperidinediol (Compound 7) from (3R,4R,5R,)-3-benzyloxy-5-hydroxymethyl-1-methyl-piperidin-4-ol. The crude product was purified on silica gel (Eluent:ethanol/25% ammonium hydroxide) resulting in 21% yield of (3R,4R,5R)-5-hydroxymethyl-1-methyl-3,4-piperidinediol isolated as the hydrochloride as a hard oil.

MS(El): m/e (Rel.Int %): 161(20)M+, 144(31), 126(13),100 (16), 70(16), 58(16), 44(100).

(3R,4R,5R)-5-Hydroxymethyl-1-methoxy-3,4-piperidinediol (Compound 8) from (3R,4R,5R,)-3-benzyloxy-5-hydroxymethyl-1-methoxy-piperidin4-ol.
MS(SP): m/e 177 (M⁺).

EXAMPLE 5

(3R,4R,5R)-5-Hydroxymethyl-1-(4-N,N-diphenylaminobenzyl)-3,4-piperidinediol (Compound 9)

(3R,4R,5R)-5-Hydroxymethyl-3,4-piperidindiol (0.1 g, 0.7 mmol) was mixed with 4-N,N-diphenylaminobenzaldehyde (0.2 g, 0.7 mmol) and sodium cyanoborohydride (0.04 g, 0.6 mmol) in methanol (5 ml). The mixture was stirred at room temperature for 100 h, acidified to pH=2 with concentrated hydrochloric acid and evaporated to dryness. The residue was dissolved in water, pH adjusted to 10 with aqueous sodium hydroxide and the solution extracted with methylene chloride. The organic phase was dried over magnesium sulphate, evaporated in vacuo. Purification of the complex mixture on silica gel using methanol as eluent gave (3R,4R,5R)-5-hydroxymethyl-1-(4-N,N-diphenylaminobenzyl)-3,4-piperidinediol as an oil (Yield: 1%).

¹H-NMR (CD₃OD) in ppm: d 1.8 (m, 3H), 2.9–3.15 (m, 3H), 3.5 (m, 4H), 3.8 (dd, 1H), 6.9–7.3 (m, 14H). ¹³C-NMR (CD₃OD) in ppm: d 55.38, 58.34, 61.72, 62.01, 72.22, 123.01, 123.73, 124.32, 129.35, 130.69, 131.59.

EXAMPLE 6

(3R,4R,5R)-1-Acetyl-5-hydroxymethyl-3,4-piperidinediol (Compound 10)

(3R,4R,5R)-3-Benzyloxy-5-hydroxymethyl4-piperidinol (0.1 g, 0.4 mmol) was dissolved in pyridine (0.5 ml) at 0° C. by and acetic anhydride (0.5 ml) was added dropwise over 1 min. Stirring at room temperature for 20 h and evaporation to dryness gave a crude product which was purified on silica gel using ethanol as eluent (yield 55%). The purified 3-benzyloxy-3-acetoxy-5-acetoxymethyl-1-acetylpiperidine (75 mg) was debenzylated in methanol at room temperature using 10% Pd/C as catalyst. Filtration and evaporation to dryness gave 50 mg of crude 4-acetoxy-5-acetoxymethyl-1-acetyl-3-piperidinol which was dissolved in dry methanol (4 ml) containing 50 µl of a 1% sodium methoxide in methanol. After stirring at room temperature for 4 days the solution was evaporated to dryness to give (3R,4R,5R)-1-acetyl-5-hydroxymethyl-3,4-piperidinediol (Yield: 35 mg).

¹H-NMR (CD₃OD) in ppm: d 1.6 (m, 1H. H-5), 2.1 (s, 3H. O-Me), 2.4–2.7 (m, 1H. H-6$_{ax}$), 2.8-3.1 (m, 1H. H-4), 3.2–3.4 (m, 2H. H-2), 3.5–3.7 (m, 1H. H-5'), 3.7–4.1 (m, 2H. H-5'+H-3), 4.4–4.6 (m, 1H. H-6$_{eq}$). ¹³C-NMR (CD₃OD) in ppm: d 24.11, 24.16, 47.01, 48.17, 49.17, 50.14, 51.54, 51.78, 51.98, 54.81, 64.75, 64.84, 75.28, 75.88, 78.14, 78.36.

EXAMPLE 7

Methyl 1-methyl-1,2,3,6-tetrahydropyridine-3-carboxylate

Arecoline (15.5 g, 0.1 mol) in tetrahydrofuran (200 ml) was added to a solution of diisopropylamine (18.1 g, 0.18 mol) in tetrahydrofuran (150 ml) and 1.5M n-butyllithium in hexane (108 ml, 0.16 mol) using the procedure described in Aust. J. Chem. 36(1983) 601–608. The reaction mixture was stirred at −10° C. for 20 min, cooled to −60 ° C. and poured into a solution of 10% aqueous hydrochloric acid (185 ml).

Work up as described in the literature gave 14 g of a crude product, which was purified by distillation in vacuo (bp. 85° C. /0.1 bar) to give methyl 1-methyl-1,2,3,6-tetrahydropyridine-3-carboxylate (Yield: 6.8 g).

¹³C-NMR (CDCl3) in ppm: δ42.35, 46.07, 52.30, 54.48, 122.86, 127.78, 173.2.

EXAMPLE 8

(1-Methyl-1,2,3,6-tetrahydro-3-pyridyl)methanol

A solution of methyl 1-methyl-1,2,3,6-tetrahydropyridine-3-carboxylate (88 g, 0.56 mol) dissolved in dry diethyl ether (250 ml) was slowly added to a slurry of lithium aluminium hydride (23 g, 0.6 mol) in diethyl ether (500 ml). The mixture was refluxed for 30 min. Water (100 ml) and potassium carbonate (100 g, 0.72 mol) were added carefully and the mixture was filtered and evaporated to dryness in vacuo. The residue was distilled in vacuum giving one pure fraction of (1-methyl-1,2,3,6-tetrahydro-3-pyridyl)methanol (Yield:15 g). (bp 38–40° C./0.2 bar).

Two more fractions (total yield: 53.8 g) were collected for later re-distillation. (bp 40–60° C./0.2 bar).

¹³C-NMR (CDCl₃) in ppm: δ36.59, 45.09, 53.92, 56.46, 66.10, 125.43, 126.86. ¹H-NMR (CDCl₃) in ppm:δ2.3 (s, 3H), 2.3 (d, 1H), 2.5 (d.d., 1H), 2.7(m, 1H), 2.8(d.d., 1H), 3.15(d.d., 1H), 3.7(m, 1H), 3.8(d.d., 1H), 5.7 (m, 1H), 5.9(m, 1H).

EXAMPLE 9

Methyl 1-benzyloxycarbonyl-1,2,5,6-tetrahydropyridine-3-carboxylate

Arecoline (39.5 g, 0.25 mol) was dissolved in dry toluene (20 ml). 1-Chloroethyl chloroformate (30.5 ml) was added slowly at 0–5° C. The mixture was heated at 80° C. for 2 h, cooled to room temperature, filtered and evaporated to dryness in vacuo. The residue was dissolved in methylene chloride (400 ml) and extracted with 10% aqueous sodium carbonate. The organic layer was dried over magnesium sulfate, filtered and evaporated to dryness to give methyl 1,2,5,6-tetrahydropyridine-3-carboxylate (Yield: 30.5 g, 85%). Methyl 1,2,5,6-tetrahydropyridine-3-carboxylate (1.1 g, 7.8 mmol) was dissolved in methylene chloride (20 ml) and cooled to −15° C. Triethyl amine (2.2 ml, 15,8 mmol) and a solution of benzyl chloroformate (1.2 ml, 8,4 mmol) in methylene chloride (10 ml) were added. Stirring at room temperature for 1.5 h followed by evaporation to dryness. The residue was dissolved in methylene chloride and extracted with water two times. The organic layer separated, dried and evaporated to dryness in vacuo to give methyl 1-benzyloxycarbonyl-1,2,5,6-tetrahydropyridine-3-carboxylate as an oil (Yield: 2.0 g, 92%).

¹H-NMR (CDCl₃) in ppm:δ7.35 (m, 5H), 7.08 (m, 1H), 5.15 (s, 2H) ,4.17 (d.d., 2H), 3.75 (s, 3H), 3.55 (t, 2H), 2.31 (m, 2H).

EXAMPLE 10
(1-Benzyloxycarbonyl-1,2,3,6-tetrahydro-3-pyridyl)methanol

Methyl 1-benzyloxycarbonyl-1,2,5,6-tetrahydropyridine-3-carboxylate (1 g, 3.6 mmol) was isomerised and reduced using the methods described in example 7 and 8 to give (1-benzyloxycarbonyl-1,2,3,6-tetrahydro-3-pyridyl)methanol (Yield: 0.32 g, 36%).

$^1$H-NMR (CDCl$_3$) in ppm: δ7.28 (m, 5H), 5.68 (m, 2H), 5.10 (s, 2H), 3.87 (m, 2H), 3.7–3.3 (m, 5H), 2.48 (m, 1H). $^{13}$C-NMR (CDCl3) in ppm: d 156.56, 156.07, 137.04, 128.93, 128.46, 128.23, 126.96, 126.14, 125.60, 72.29, 70.87, 67.66, 63.52, 59.38, 44.13, 43.14, 42.67, 38.51.

EXAMPLE 11
Methyl 1-tert-butoxycarbonyl-1,2,5,6-tetrahydropyridine-3-carboxylate Methyl 1,2,5,6-tetrahydropyridine-3-carboxylate (20.44 g, 145 mmol) and triethylamine (25 ml, 180 mmol) were dissolved in methanol (250 ml) and di-tert-butyl dicarbonate (65.48 g, 300 mmol) was added at room temperature. The mixture was heated at 60 ° C. for 30 min., evaporated to dryness and partitioned between water and ethyl acetate. The organic layer was isolated, dried over magnesium sulphate and evaporated to dryness in vacuo. Purification on silicagel (Eluent: methylene chloride/methanol (19/1)) gave methyl 1-tert-butoxycarbonyl-1,2,5,6-tetrahydropyridine-3-carboxylate as a yellow oil.(Yield: 34.9 g, 99%) $^{13}$C-NMR (CDCl$_3$) in ppm: δ166.20, 155.14, 138.30, 128.5, 80.37, 52.07, 42.96, 28.81, 25.91. $^1$H-NMR (CDCl$_3$) in ppm: δ7.08 (1H,m), 4.10 (2H,m), 3.75 (3H,s), 3.48 (2H,t), 2.32 (2H,m) 1.48 (9H,s).

EXAMPLE 12
1-tert-Butoxycarbonyl-1,2,5,6-tetrahydropyridine-3-carboxylic acid A solution of potassium hydroxide (44 g, 0.79 mol) in water (450 ml) was added to a solution of methyl 1-tert-butoxycarbonyl-1,2,5,6-tetrahydropyridine-3-carboxylate (34.9 g, 145 mmol) in methanol (450 ml). The mixture was refluxed for 3h and evaporated to dryness in vacuo. The residue acidified to pH 2.5 with hydrochloric acid (4M) and extracted with methylene chloride. The organic layer was dried over magnesium sulphate and evaporated to dryness in vacuo to give 1-tert-butoxycarbonyl-1,2,5,6-tetrahydropyridine-3-carboxylic acid. (Yield: 28.4g, 86%) m.p. 198–202° C. $^{13}$C-NMR (DMSO-d$_6$) in ppm: δ167.16, 154.77, 138.19, 129.26, 79.91, 43.14, 28.92, 25.81

EXAMPLE 13
1-tert-Butoxycarbonyl-1,2,3,6-tetrahydropyridine-3-carboxylic acid A solution of 1-tert-butoxycarbonyl-1,2,5,6-tetrahydropyridine-3-carboxylic acid (6.5 g, 28.6 mmol) in dry tetrahydrofuran (150 ml) was added dropwise to a mixture of 2.5 M butyllithium in hexane (25 ml, 62.5 mmol) and diisopropylamine (6.37 g, 63.1 mmol) in dry tetrahydrofuran (150 ml) at <−65° C. Stirring was continued for 20 min. −10°C. The mixture was poured into 1 M aqueous HCl (100 ml) while cooling with ice. The resulting mixture was extracted several times with ethyl acetate (a total of 500 ml). The organic layer was dried over magnesium sulphate and evaporated to dryness in vacuo to give 1-tert-butoxycarbonyl-1,2,3,6-tetrahydropyridine-3-carboxylic acid (Yield: 6.3 g, 97%).

$^1$H-NMR (CDCl$_3$) in ppm: δ5.8–6.0 (m, 2H), 3.8–4.0 (m, 3H), 3.5–3.7 (m, 1H), 3.2–3.3 (m,1H), 1.48 (s, 9H); $^{13}$C-NMR (CDCl$_3$) in ppm: δ177.5, 155.24, 127.36 (m), 123.09, 80.83, 43.43 (m), 42.39 (m), 41.21, 28.77.

EXAMPLE 14
Methyl 1-tert-butoxycarbonyl-1,2,3,6-tetrahydropyridine-3-carboxylate 1,1'-Carbonyldiimidazole (4 g, 24.7 mmol) in methylene chloride (100 ml) was added dropwise to a solution of 1-tert-butoxycarbonyl-1,2,3,6-tetrahydropyridine-3-carboxylic acid (5 g, 22 mmol) in methylene chloride (200 ml) under a nitrogen atmosphere. Stirring was continued for 1 h followed by addition of methanol (300 ml), and reflux for 26 h. 10% aqueous citric acid (100 ml) was added and the mixture extracted with methylene chloride. The organic layer was dried over magnesium sulphate, evaporated to dryness in vacuo and purified on a silica gel column (Eluent: methylene chloride/methanol (90/1)) to give methyl 1-tert-butoxycarbonyl-1,2,3,6-tetrahydropyridine-3-carboxylate as yellow oil. (Yield: 3.9 g, 73%)

$^{13}$C-NMR (CDCl$_3$) in ppm. δ172.65, 155.04, 127.0 (m), 123.44(m), 80.34, 52.47, 51.69, 41.38, 28.80, 28.55; $^1$H-NMR (CDCl$_3$) in ppm: δ5.8–6.0 (m, 2H), 3.7–4.1 (m, 2H), 3.7 (s, 3H) 3.5–3.6 (m, 2H), 3.2–3.3 (m, 1H), 1.48 (s, 9H).

EXAMPLE 15
1-tert-Butoxycarbonyl-1,2,3,6-tetrahydropyridyl-3-methanol

Methyl 1-tert-butoxycarbonyl-1,2,3,6-tetrahydropyridine-3-carboxylate (2.35 g, 9.8 mmol) was dissolved in dry diethyl ether (200 ml) under a nitrogen atmosphere. Lithium borohydride (0.6 g, 27.5 mmol) and 1.0 M lithium triethylborohydride in tetrahydrofuran (3 g, 28.3 mmol) were slowly added. The resulting mixture was refluxed for 1 h, poured into 1 M sodium hydroxide (100 ml) and extracted with methylene chloride. The organic layer was dried over magnesium sulphate, evaporated to dryness in vacuo and purified on a silica gel column (Eluent: methylene chloride/methanol (19/1)) to give 1-tert-butoxycarbonyl-1,2,3,6-tetrahydropyridyl-3-methanol as a colourless oil (Yield: 1.28 g, 61%)

MS(El): m/e 213 (M$^+$).

$^1$H-NMR (CDCl$_3$) in ppm: δ5.71 (m, 2H), 3.95–4.1 (m, 1H), 3.7–3.9 (m, 1H), 3.2–3.7 (m,3H), 2.35–2.45 (m, 1H), 2.12 (t, 1H), 1.8–1.9 (m, 1H), 1.48 (s, 9H). $^{13}$C-NMR (CDCl$_3$) in ppm: δ156.0 (m), 126.7 (m), 80.37, 63.5 (m), 44.6 (m), 42.7 (m), 38.57, 28.81.

EXAMPLE 16
tert-Butyl 3-((1R,2S,5R)-2-isopropyl-5-methyl-1-cyclohexyloxy)acetoxymethyl-1,2,3,6-tetrahydropyridine-1-carboxylate.

(−)-Menthoxyacetyl chloride (1.03 g, 4.4 mmol) was slowly added to a solution of 1-tert-butoxycarbonyl-1,2,3,6-tetrahydropyridyl-3-methanol (0.59 g, 2.8 mmol) in methylene chloride (50 ml) under a nitrogen atmosphere. The mixture was refluxed for 4 h, evaporated to dryness in vacuo and purified on a silica gel column (Eluent: methyl tert-butylether/methylene chloride (1/20)) to give a diastereomeric mixture of tert-butyl 3-((1R,2S,5R)-2-isopropyl-5-methyl-1-cyclohexyloxy)acetoxymethyl-1,2,3,6-tetrahydropyridine-1-carboxylate as an colourless oil (Yield: 0.54 g, 48%).

A minor amount of the two isomers were separated on a chiral column (chiracel; eluent: isopropyl alkohol/ heptane (5/95))(Rt 9.6 min and 11.2 min).

MS: m/e 409 (M$^+$).

$^{13}$C-NMR (CDCl$_3$) in ppm: δ171.18, 155.34, 127.7 (m), 127.1 (m), 125.3 (m), 80.67, 80.59, 80.20, 66.29, 66.23, 65.33, 48.51, 43.4(m), 42.9 (m), 40.35, 35.36, 34.81, 31.90, 28.82, 25.87, 23.68, 22.69, 21.38, 16.68.

EXAMPLE 17
tert-Butyl 3-((1R,2S,5R) 2-isopropyl-5-methyl-1-cyclohexyloxy)acetoxymethyl-4.5-epoxypiperidine-1-carboxylate A solution of 3-chloroperoxybenzoic acid (0.9 g, 5.2 mmol), tert-butyl 3-((1R,2S,5R)-2-isopropyl-5-methyl-1-cyclohexyloxy)acetoxymethyl-1,2,3,6-tetrahydropyridine-1-carboxylate (0.5 g, 1.2 mmol), and methylene chloride (150 ml) was stirred at room temperature for 20 h. An extra portion of 3-chloroperoxybenzoic acid (1.1 eq) was added and the mixture refluxed for 2h. The reaction mixture was extracted with 1M sodium hydroxide and water, dried over magnesium sulphate and evaporated to dryness in vacuo. The residue was purified on a silica gel column (Eluent: heptane/ethyl acetate (5/1)) to give tert-butyl 3-((1R,2S,5R) 2-isopropyl-5-methyl-1-cyclohexyloxy)acetoxymethyl-4,5-epoxypiperidine-1-carboxylate as an oil (Yield: 0.34 g, 66%).

$^{13}$C-NMR (CDCl$_3$) in ppm: δ173.16, 157.08, 82.71, 82.61, 68.28, 66.27, 65.78, 54.43, 53.9, 52.99, 52.35, 50.54, 44.5 (broad), 42.38, 41.22, 36,82, 33.92, 32.13, 30.77, 27.93, 25.72, 25.1, 23.4, 18.72.

In a similar way the following compounds were prepared:
tert-Butyl 3-hydroxymethyl-4,5-epoxypiperidine-1-carboxylate was prepared from 1-tert-butoxycarbonyl-1,2,3,6-tetrahydropyridyl-3-methanol $^1$H-NMR (CDCl$_3$) in ppm: δ3.6–4.0 (m, 4H); 3.35 (t, 1H); 3.1–3.3 (m, 3H); 2.23 (m,1H); 1.48 (s, 9H).
Benzyl 3-hydroxymethyl-4,5-epoxypiperidine-1-carboxylate from (1-benzyloxycarbonyl-1,2,3,6-tetrahydro-3-pyridyl)methanol $^{13}$C-NMR (CDCl$_3$) in ppm: δ156.21, 155.84, 136.86, 128.95, 128.53, 128.27, 128.24, 67.80, 62.48, 62.13, 61.55, 52.94, 52.40, 50.91, 50.48, 42.99, 42.74, 40.17, 37.56, 37.19, 36.92. $^1$H-NMR (CDCl$_3$) in ppm: δ7.3 (m, 5H), 5.06 (s, 2H), 4.0–2.9 (m, 9 H), 2.32 (m,¼H), 2.20(m, ¾H). The NMR signals indicates a mixture of two isomers ratio approx.⅓.

EXAMPLE 18
5-Hydroxymethyl-3,4-piperidinediol tert-Butyl 3-((1R,2S,5R)-2-isopropyl-5-methyl-1-cyclohexyloxy)acetoxymethyl-4,5-epoxypiperidine-1-carboxylate (0.25 g, 0.59 mmol) and 10% aqueous potassium hydroxide were refluxed for 3h. The reaction mixture was evaporated to dryness in vacuo and purified on a silica gel column (Eluent: isopropyl alkohol /26% ammonium hydroxide (3/1)) to give 5-hydroxymethyl-3,4-piperidinediol as an oil (Yield: 56 mg, 65%).

Chiral TLC (Machery-Nagel 811058 plates; eluent: isopropyl alkohol /26% ammonium hydroxide (3/1)) showed two isomers Rf 0.55 resp 0.59.
MS: m/e 147 (M$^+$).

$^{13}$C-NMR (D$_2$O) in ppm: δ71.52, 68.94, 65.64, 65.54, 60.59, 59.38, 47.03, 45.20, 44.57, 41.44, 40.98, 35.26.

In a similar way 5-hydroxymethyl-3,4-piperidinediol was prepared from tert-butyl 3-hydroxymethyl-4,5-epoxypiperidine-1-carboxylate or from benzyl 3-hydroxymethyl-4,5-epoxypiperidine-1-carboxylate.

In a similar way 5-hydroxymethyl-1-methyl-3,4-piperidinediol was prepared from (1-methyl-1,2,3,6-tetrahydro-3-pyridyl)methanol.

EXAMPLE 19
(1-Methyl-1,2,3,6-tetrahydro-3-pyridyl)methanol

1M Lithium triethylborohydride in tetrahydrofuran (75ml, 75 mmol) was slowly added to a solution of methyl 1-methyl-1,2,3-6-tetrahydropyridine-3-carboxylate (5 g, 31.8 mmol) in dry tetrahydrofuran ( 200 ml). The mixture was refluxed for 3h, cooled to room temperature and poured into 1M aqueous hydrochloric acid (150 ml). The aqueous layer was extracted with methylene chloride and pH was adjusted to 9 with aqueous sodium hydroxide. The solution was extracted with methylene chloride, which was dried over magnesium sulfate and evaporated to dryness in vacuo. The residue was distilled in Kugelrohr (bp: 65–75° C./0.28 mbar) to give (1-methyl-1,2,3,6-tetrahydro-3-pyridyl) methanol as an oil (Yield: 1.9 g, 48%)

$^{13}$C-NMR (CDCl$_3$): in ppm: δ127.28, 126.34, 66.94, 57.31, 54.83, 46.00, 37.58.

EXAMPLE 20
1-Methyl-1,2,3,6-tetrahydropyridin-3-yl acetate.

A solution of (1-methyl-1,2,3,6-tetrahydro-3-pyridyl) methanol (0.7 g, 5.5 mmol), triethylamine (25 ml), and acetic anhydride (20 ml) was refluxed for 2h. The reaction mixture was extracted with methylene chloride and pH was adjusted to 10 with aqueous sodium hydroxide. The solution was extracted with methylene chloride, which was dried over magnesium sulfate and evaporated to dryness in vacuo. The residue was purified on a silica gel column (Eluent: methanol/methylene chloride (1/9)) to give 1-methyl-1,2,3, 6-tetrahydropyridin-3-yl acetate as an oil (Yield: 0.69 9, 70%).

A minor amount of the two enantiomers were separated on chiral HPLC (chiracel OD 250×4.6 mm; eluent: isopropyl alcohol/heptane (1/99); RT 16 min and 18 min).

$^{13}$C-NMR (CDCl$_3$) in ppm: δ171.44, 127.97, 125.15, 66.56, 55.13, 54.95, 46.33, 36.48, 21.34. $^1$H-NMR (CDCl$_3$) in ppm: δ5.78 (m, 1H), 5.61 (m, 1H), 4.0 (m, 2H), 2.91 (m, 2H), 2.64 (m, 2H), 2.35 (s, 3H), 2.28 (m, 1H), 2.06 (s, 3H).

EXAMPLE 21
(3R,4R,5R)-5-Hydroxymethyl-1-(3-phenylallyl)-3.4-piperidinediol (Compound 11)

To a suspension of Wang resin (10 g, 9.2 mmol, Bachem, loading: 0.92 mmol/g) in methylene chloride were added N,N-diisopropylethylamine (15 ml, 87.8 mmol) and acryloyl chloride (10 ml, 122.7 mmol). After stirring slowly for 7 h the mixture was filtered and the resin washed with methylene chloride (500 ml) and methanol (500 ml). Drying in vacuo gave Wang resin—O—CO—CH=CH$_2$ (Yield: 9.4 g).

To a suspension of this resin (4 g, 3.7 mmol) in DMF (30 ml) was added a solution of (3R,4R,5R)-5-hydroxymethyl-3,4-piperidinediol (0.9 g, 6.1 mmol) in DMF (5 ml). The mixture was shaken for 22 h, filtered and the resin washed with DMF (4×25 ml), methylene chloride (4×25 ml) and methanol (4×25 ml). The resin was dried in vacuo to give approx. 4.1 g material.

3-Bromo-1-phenyl-1-propene (180 mg, 0.91 mmol) was added to a suspension of this resin (190 mg, 0.17 mmol) in DMF (5 ml). The mixture was shaken for 24 h, filtered and the resin washed with DMF (5×5 ml), methylene chloride (3×5 ml) and DMF (2×5 ml). N,N-Diisopropylethylamine (0.125 ml, 0.73 mmol) and DMF (3 ml) was added to the resin. The mixture was shaken for 24 h, filtered and the filtrate was concentrated to dryness in vacuo to give (3R, 4R,5R)-5-hydroxymethyl-1-(3-phenylallyl)-3,4-piperidinediol as an oil (Yield: 35 mg, 78%).
LC-MS: m/e 264 (MH$^{30}$ )

$^1$H-NMR (CD$_3$OD) in ppm: δ7.5 (d, 2H); 7.3(m, 3H); 6.9 (d, 1H);6.35 (d.t., 1H); 3.9 (d, 2H); 3.8 (d.d., 1H); 3.7 (m, 2H); 3.55 (m, 2H); 3.4 (t, 1H); 2.76–3.0 (m, 2H); 1.95 (m, 1H).

In a similar way the following compounds were prepared:

(3R,4R,5R) 1-Allyl-5-hydroxymethyl-3,4-piperidinediol (Compound 12) from (3R,4R,5R)-5hydroxymethyl-3,4-piperidinediol and allyl bromide.

LC-MS: m/e 188 (MH$^+$)

$^1$H-NMR (CD$_3$OD) in ppm: δ5.9–6.1 (m, 1H); 5.5–5.7 (m, 2H); 3.3–3.9 (m, 8H); 2.7–3.0 (m, 2H); 1.95 (m, 1H). $^{13}$C-NMR (CD$_3$OD) in ppm: δ127.99; 126.77; 72.70; 70.14; 60.71; 60.41; 55.93; 43.12.

(3R,4R,5R) 1-Benzyl-5-hydroxymethyl-3,4-piperidinediol (Compound 13) from (3R,4R,5R)-5-hydroxymethyl-3,4-piperidinediol and benzyl bromide.

LC-MS: m/e 238 (MH$^+$).

$^1$H-NMR (CD$_3$OD) in ppm: δ7.5 (m, 5H); 4.24 (s, 2H); 3.6–3.9 (m, 3H); 3.3–3.5 (m, 3H); 2.7–3.0 (m, 2H); 1.95 (m, 1H).

(3R,4R,5R)-1-Octyl-5-hydroxymethyl-3,4-piperidinediol (Compound 14) from (3R,4R,5R)-5-hydroxymethyl-3,4-piperidinediol and 1-iodooctane.

LC-MS: m/e 260 (MH$^+$).

(3R,4R,5R)-2-(3,4-Dihydroxy-5-hydroxymethyl-piperidin-1-yl)-acetamide (Compound 15) from (3R,4R,5R)-5-hydroxymethyl-3,4-piperidinediol and 2-bromoacetamide.

LC-MS: m/e 205 (MH$^+$).

Ethyl ((3R,4R,5R)-3,4-dihydroxy-5-hydroxymethyl-piperidin-1-yl)acetate (Compound 16) from (3R,4R,5R)-5-hydroxymethyl-3,4-piperidinediol and ethyl bromoacetate.

LC-MS: m/e 234 (MH$^+$).

(3R,4R,5R)-5-Hydroxymethyl-1-(4-trifluoromethyl-benzyl)-3,4-piperidinediol (Compound 17) from (3R,4R,5R)-5-hydroxymethyl-3,4-piperidinediol and 4-trifluoromethylbenzyl bromide.

LC-MS: m/e 306 (MH$^+$). (3R,4R,5R)-1-(2-(4'-Fluoroacetophenone))-5-hydroxymethyl-3,4-piperidinediol (Compound 18)from (3R,4R,5R-5-hydroxymethyl-3,4-piperidinediol and 2-bromo-4'-fluoroacetophenone.

LC-MS: m/e 284 (MH$^+$).

(3R,4R,5R)-5-hydroxymethyl-1-(2-(4'-methoxyacetophenone))-3,4-piperidinediol (Compound 19)from (3R,4R,5R)-5-hydroxymethyl-3,4-piperidinediol and 2-bromo-4'-methoxyacetophenone.

LC-MS: m/e 296 (MH$^+$).

(3R,4R,5R)-1-(2-(4-Fluorophenoxy)-ethyl)-5-hydroxymethyl-3,4-piperidinediol (Compound 20)from (3R,4R,5R)-5-hydroxymethyl-3,4-piperidinediol and 4-fluorophenyl 2-bromoethyl ether.

LC-MS: m/e 286 (MH$^+$).

(3R,4R,5R)-5-Hydroxymethyl-1-(4-phenoxy-butyl)-3,4-piperidinediol (Compound 21) from (3R,4R,5R)-5-hydroxymethyl-3,4-piperidinediol and 4-phenoxybutyl bromide.

LC-MS: m/e 296 (MH$^+$).

(3R,4R,5R)-1-(4-Cyanobutyl)-5-hydroxymethyl-3,4-piperidinediol (Compound 22) from (3R,4R,5R)-5-hydroxymethyl-3,4-piperidinediol and 5-bromovaleronitrile.

LC-MS: m/e 229 (MH$^+$).

(3R,4R,5R)-1-(10-decylphthalimido)-5-hydroxymethyl-3,4-piperidinediol (Compound 23) from (3R,4R,5R)-5-hydroxymethyl-3,4-piperidinediol and N-(10-bromodecyl) phthalimide.

LC-MS: m/e 233 (MH$^+$).

(3R,4R,5R)-12-(3,4-Dihydroxy-5-hydroxymethyl-piperidin-1-yl)-dodecanoic acid (Compound 24 from (3R,4R,5R)-5-hydroxymethyl-3,4-piperidinediol and 12-bromododecanoic acid.

LC-MS: m/e 346 (MH$^+$). (3R,4R,5R)-5-Hydroxymethyl-1-phenoxyethyl-3,4-piperidinediol (Compound 25) from (3R,4R,5R)-5-hydroxymethyl-3,4-piperidinediol and 2-bromoethyl phenyl ether.

LC-MS: m/e 268 (MH$^+$).

EXAMPLE 22

(3R,4R,5R)-3-(3,4-Dihydroxy-5-hydroxymethyl-piperidin-1-yl)propionic acid (Compound 26)

To a suspension of Wang resin—O—CO—CH═CH$_2$ (2.0 g, 1.84 mmol) in DMF (15 ml) was added a solution of (3R,4R,5R)-5-hydroxymethyl-3,4-piperidinediol (0.8 g, 5.4 mmol) in DMF (3 ml). The mixture was shaken for 22 h, filtered and the resin washed with DMF (2×20 ml), methanol (3×20 ml), DMF (2×20 ml), methylene chloride (2×20 ml) and methanol (2×20 ml). The resin was dried in vacuo to give approx. 2.2 g material.

To a suspension of this resin (0.5 g, 0.46 mmol) in methylene chloride (5 ml) was added trifluoroacetic acid (5 ml). The mixture was shaken for 20 min., filtered and the filtrate was evaporated to dryness in vacuo to give (3R,4R,5R)-3-(3,4-Dihydroxy-5-hydroxymethyl-piperidin-1-yl) propionic acid as a yellow oil (Yield: 40 mg, 40%).

LC-MS: m/e 220 (MH$^+$).

$^1$H-NMR (CD$_3$OD) in ppm: δ3.3–3.9 (m, 8H); 2.8–3.1(m, 4H); 1.95 (m, 1H).

EXAMPLE 23

(3R,4R,5R)-3-Benzyloxy-5-hydroxymethyl-1-(2,3,4-tri-O-benzyl-6-deoxy-1-O-methyl-6-α-D-glucopyranosyl)4-pipendinol (3R,4R,5R)-3-Benzyloxy-5-hydroxymethyl4-piperidinol (0.25 g, 0.54 mmol) and methyl 2,3,4-td-O-benzyl-α-D-glucohexadialdose-1,5-pyranoside (0.128 g, 5.4 mmol) were dissolved in ethanol (50 ml) and palladium on carbon (10%, 30 mg) was added. The mixture was hydrogenated at 6 atm. H$_2$-pressure for 24 h, filtered through celite and concentrated in vacuo. Purification on a silica gel column (Eluent: ethyl acetate/methanol (9/1)) gave (3R,4R,5R)-3-benzyloxy-5-hydroxymethyl-1-(2,3,4-tri-O-benzyl-6-deoxy-1-O-methyl-6-α-D-glucopyranosyl)-4-piperidinol as an oil (Yield: 71 mg, 19%).

$^1$H-NMR (CDCl$_3$) in ppm: δ7.3 (m, 20H); 5.0 (d, 1H); 4.9 (d, 1H); 4.8(d.d., 2H); 4.5–4.7 (m, 3H); 4.48 (d, 1H); 4.0 (t, 1H); 3.8 (t, 1H); 3.5–3.7 (m, 2H); 3.47 (d.d., 1H);3.35 (s, 3H); 3.2–3.4 (m, 3H); 2.5–2.8 (m, 4H); 1.8–2.0 (m, 4H).

EXAMPLE 24

(3R,4R,5R)-1-(6-Deoxy-1-O-methyl-6-α-D-glucopyranosyl)-5-hydroxymethyl-3,4-piperidinediol (Compound 27)

(3R,4R,5R)-3-Benzyloxy-5-hydroxymethyl-1-(2,3,4-tri-O-benzyl-6-deoxy-1-O-methyl-6-α-D-glucopyranosyl)4-piperidinol (71 mg, 0.1 mmol) was dissolved in ethanol (20ml) containing aqueous hydrochloric acid (4N, 0.3 ml), and palladium on carbon (10%, 50 mg) was added. The mixture was hydrogenated at 1 atm. H$_2$-pressure for 3h, filtered through celite and concentrated in vacuo. Purification on a silica gel column (Eluent: ethanol/25% ammonium hydroxide (9/1)) gave the free base of (3R,4R,5R)-1-(6-deoxy-1-O-methyl-6-α-D-glucopyranosyl)-5-hydroxymethyl-3,4-piperidinediol as a yellow oil (Yield: 21 mg, 64%).

LC-MS: m/e 324 (MH$^+$).

$^1$H-NMR (CD$_3$OD) in ppm: 4.64 (d, 1H); 3.7–3.9 (m, 2H); 3,5–3.7 (m, 4H); 3,43 (s, 3H); 3.37 (d.d., 1H); 3.05–3.25 (m, 3H); 2.37 (d.d., 1H); 2.6 (d.d., 1H); 2.03 (q, 2H); 1,75 (m, 1H).

We claim:

1. A compound of formula I:

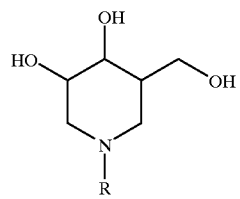

(I)

wherein

R is straight or branched $C_{1-6}$-alkoxy; or R is straight or branched $C_{1-18}$-alkyl, $C_{2-18}$-alkene, or $C_{2-18}$-alkyne each of which is optionally substituted with cyano, carboxylic acid, trifluoromethyl, hydroxy, perhalomethyl, halogen, $C_{3-7}$-cycloalkyl, $C_{1-6}$-alkoxy, $C_{1-6}$-alkoxycarbonyl, benzyloxycarbonyl, or —$NR_1R_2$ wherein $R_1$ and $R_2$ independently are hydrogen, $C_{1-6}$-alkyl, or benzyl; or R is straight or branched $C_{1-18}$-alkyl, $C_{2-18}$-alkene, or $C_{2-18}$-alkyne each of which is optionally substituted with —$SR_3$ wherein $R_3$ is $C_{1-6}$-alkyl, phenyl or carbonyl($C_{1-6}$-alkyl); or R is straight or branched $C_{1-18}$-alkyl, $C_{2-18}$-alkene, or $C_{2-18}$-alkyne each of which is optionally substituted with carbonyl ($C_{1-6}$-alkyl) or carbonylphenyl, which are optionally substituted with methoxy, nitro, halogen, or cyano; or R is straight or branched $C_{1-18}$-alkyl, $C_{2-18}$-alkene, or $C_{2-18}$-alkyne each of which is optionally substituted with phenoxy or phenyl, which are optionally substituted with trifluoromethyl, methoxy, $C_{1-6}$alkyl, carboxylic acid, nitro, cyano, halogen, phenyl, methoxycarbonyl, or methylsulfonyl; or R is straight or branched $C_{1-18}$-alkyl, $C_{2-18}$-alkene, or $C_{2-18}$-alkyne each of which is optionally substituted with —$CONR_4R_5$, wherein $R_4$ and $R_5$ independently are hydrogen or $C_{1-6}$-alkyl; or R is $C_{3-7}$-cycloalkyl optionally substituted with cyano, carboxylic acid, hydroxy, oxo, perhalomethyl, halogen, phenyl, $C_{1-6}$-alkoxy, $C_{1-6}$-alkoxycarbonyl, benzyloxycarbonyl, hydroxy-$C_{1-6}$-alkyl, $C_{1-6}$-alkyl or —$NR_1R_2$ wherein $R_1$ and $R_2$ independently are hydrogen, $C_{1-6}$-alkyl, or benzyl, or a pharmaceutically acceptable salt thereof.

2. A compound of claim 1 wherein R is straight or branched $C_{1-6}$-alkoxy.

3. A compound of claim 1 wherein R is straight or branched $C_{1-18}$-alkyl, $C_{2-18}$-alkene, or $C_{2-18}$-alkyne each of which is optionally substituted with cyano, carboxylic acid, trifluoromethyl, hydroxy, perhalomethyl, halogen, $C_{3-7}$-cycloalkyl, $C_{1-6}$-alkoxy, $C_{1-6}$-alkoxycarbonyl, benzyloxycarbonyl, or —$NR_1R_2$ wherein $R_1$ and $R_2$ independently are hydrogen, $C_{1-6}$-alkyl, or benzyl.

4. A compound of claim 3 wherein R is straight or branched $C_{1-18}$-alkyl optionally substituted with $C_{3-7}$-cycloalkyl.

5. A compound of claim 4 wherein R is straight or branched $C_{1-18}$-alkyl substituted with cyclohexyl.

6. A compound of claim 1 wherein R is straight or branched $C_{1-18}$-alkyl, $C_{2-18}$-alkene, or $C_{2-18}$-alkyne each of which is optionally substituted with —$SR_3$ wherein $R_3$ is $C_{1-6}$-alkyl, phenyl or carbonyl($C_{1-6}$alkyl).

7. A compound of claim 1 wherein R is straight or branched $C_{1-18}$-alkyl, $C_{2-18}$-alkene, or $C_{2-18}$-alkyne each of which is optionally substituted with carbonyl($C_{1-6}$-alkyl) or carbonylphenyl, which are optionally substituted with methoxy, nitro, halogen, or cyano.

8. A compound of claim 1 wherein R is straight or branched $C_{1-18}$-alkyl, $C_{2-18}$-alkene, or $C_{2-18}$-alkyne each of which is optionally substituted with phenoxy or phenyl, which are optionally substituted with trifluoromethyl, methoxy, $C_{1-6}$-alkyl, carboxylic acid, nitro, cyano, halogen, phenyl, methoxycarbonyl, or methylsulfonyl.

9. A compound of claim 1 wherein R is straight or branched $C_{1-18}$-alkyl optionally substituted with phenyl.

10. A compound of claim 1 wherein R is straight or branched $C_{1-18}$-alkyl, $C_{2-18}$-alkene, or $C_{2-18}$-alkyne each of which is optionally substituted with —$CONR_4R_5$, wherein $R_4$ and $R_5$ independently are hydrogen or $C_{1-6}$-alkyl.

11. A compound of claim 1 wherein R is $C_{3-7}$-cycloalkyl optionally substituted with cyano, carboxylic acid, hydroxy, oxo, perhalomethyl, halogen, phenyl, $C_{1-6}$-alkoxy, $C_{1-6}$-alkoxycarbonyl, benzyloxycarbonyl, hydroxy-$C_{1-6}$-alkyl, $C_{1-6}$-alkyl or —$NR_1R_2$ wherein $R_1$ and $R_2$ independently are hydrogen, $C_{1-6}$-alkyl, or benzyl.

12. A compound of claim 1 wherein R is propyl or dodecyl.

13. A compound of claim 1 wherein R is propyl.

14. A compound of claim 1 wherein R is dodecyl.

15. A compound of claim 1 which is 1-(3-cyclohexyl)propyl)-5-hydroxymethyl-3,4-piperidinediol, or a pharmaceutically acceptable salt, optical isomer or mixture of optical isomers, or tautomeric form thereof.

16. A compound of claim 15 which is:

(3R, 4R, 5R)-1-(3-cyclohexyl)propyl)-5-hydroxymethyl-3,4-piperidinediol, (3S, 4S, 5S)-1-(3-cyclohexyl)propyl)-5-hydroxymethyl-3,4-piperidinediol, or a pharmaceutically acceptable salt or tautomeric form thereof.

17. A compound of claim 1 which is 1-dodecyl-5-hydroxymethyl-3,4-piperidinediol, or a pharmaceutically acceptable salt, optical isomer or mixture of optical isomers, or tautomeric form thereof.

18. A compound of claim 17 which is:

(3R, 4R, 5R)-1-dodecyl-5-hydroxymethyl-3,4-piperidinediol, (3S, 4S, 5S)-1-dodecyl-5-hydroxymethyl-3,4-piperidinediol, or a pharmaceutically acceptable salt or tautomeric form thereof.

19. A compound of claim 1 which is 5-hydroxymethyl-1-(3-phenylpropyl)-3,4-piperidinediol, or a pharmaceutically acceptable salt, optical isomer or mixture of optical isomers, or tautomeric form thereof.

20. A compound of claim 19 which is:

(3R, 4R, 5R)-5-hydroxymethyl-1-(3-phenylpropyl)-3,4-piperidinediol, or (3S, 4S, 5S)-5-hydroxymethyl-1-(3-phenylpropyl)-3,4-piperidinediol, or a pharmaceutically acceptable salt or tautomeric form thereof.

21. A compound of claim 1 which is:

1-butyl-5-hydroxymethyl-3,4-piperidinediol, 5-hydroxymethyl-1-methyl-3,4-piperidinediol, 1-octyl-5-hydroxymethyl-3,4-piperidinediol, or 1-(4-cyanobutyl)-5-hydroxymethyl-3,4-piperidinediol, or a pharmaceutically acceptable salt, optical isomer or mixture of optical isomers, or tautomeric form thereof.

22. A compound of claim 21 which is:

(3R, 4R, 5R)-(1-butyl-5-hydroxymethyl-3,4-piperidinediol, (3R, 4R, 5R)-5-hydroxymethyl-1-methyl-3,4-piperidinediol, (3R, 4R, 5R)-1-octyl-5-hydroxymethyl-3,4-piperidinediol, (3R, 4R, 5R)-1-4-cyanobutyl)-5-hydroxymethyl-3,4-piperidinediol, (3S, 4S, 5S)-1-butyl-5-hydroxymethyl-3,4-piperidinediol, (3S, 4S, 5S)-5-hydroxymethyl-1-methyl-3,4-piperidinediol, (3S, 4S, 5S)-1-octyl-5-hydroxymethyl-3,4-piperidinediol, or (3S, 4S, 5S)-1-(4-cyanobutyl)-5-hydroxymethyl-3,4-piperidinediol, or a pharmaceutically acceptable salt or tautomeric form thereof.

23. A compound of claim 1 which is:

5-hydroxymethyl-1-(4-phenoxy-butyl)-3,4-piperidinediol, 5-hydroxymethyl-1-phenoxyethyl-3,4-piperidinediol, (2-(4-fluorophenoxy)-ethyl)-5-hydroxymethyl-3,4-piperidinediol, 1-benzyl-5-hydroxymethyl-3,4-piperidinediol, 5-hydroxymethyl-1-(4-trifluoromethyl-benzyl)-3,4-piperidinediol, 5-hydroxymethyl-1-(3-phenylallyl)-3,4-piperidinediol, or 1-allyl-5-hydroxymethyl-3,4-piperidinediol, or a pharmaceutically acceptable salt, optical isomer or mixture of optical isomers, or tautomeric form thereof.

24. A compound of claim 23 which is:

(3R, 4R, 5R)-5-hydroxymethyl-1-(4-phenoxy-butyl)-3,4-piperidinediol, (3R, 4R, 5R)-5-hydroxymethyl-1-phenoxyethyl-3,4-piperidinediol, (3R, 4R, 5R)-(2-(4-fluorophenoxy)-ethyl)-5-hydroxymethyl-3,4-piperidinediol, (3R, 4R, 5R)-1-benzyl-5-hydroxymethyl-3,4-piperidinediol, (3R, 4R, 5R)-5-hydroxymethyl-1-(4-trifluoromethyl-benzyl)-3,4-piperidinediol, (3R, 4R, 5R)-5-hydroxymethyl-1-(3-phenylallyl)-3,4-piperidinediol, (3R, 4R, 5R)-1-allyl-5-hydroxymethyl-3,4-piperidinediol, (3S, 4S, 5S)-5-hydroxymethyl-1-(4-phenoxy-butyl)-3,4-piperidinediol, (3S, 4S, 5S)-5-hydroxymethyl-1-phenoxyethyl-3,4-piperidinediol, (3S, 4S, 5S)-(2-(4-fluorophenoxy)-ethyl)-5-hydroxymethyl-3,4-piperidinediol, (3S, 4S, 5S)-1-benzyl-5-hydroxymethyl-3,4-piperidinediol, (3S, 4S, 5S)-5-hydroxymethyl-1-(4-trifluoromethyl-benzyl)-3,4-piperidinediol, (3S, 4S, 5S)-5-hydroxymethyl-1-(3-phenylallyl)-3,4-piperidinediol, or (3S, 4S, 5S)-1-allyl-5-hydroxymethyl-3,4-piperidinediol, or a pharmaceutically acceptable salt or tautomeric form thereof.

25. A compound of claim 1 which is:

1-(2-hydroxyethyl)-5-hydroxymethyl-3,4-piperidinediol, or 5-hydroxymethyl-1-methoxy-3,4-piperidinediol, or a pharmaceutically acceptable salt, optical isomer or mixture of optical isomers, or tautomeric form thereof.

26. A compound of claim 25 which is:

(3R, 4R, 5R)-1-(2-hydroxyethyl)-5-hydroxymethyl-3,4-piperidinediol, (3R, 4R, 5R)-5-hydroxymethyl-1-methoxy-3,4-piperidinediol, (3S, 4S, 5S)-1-(2-hydroxyethyl)-5-hydroxymethyl-3,4-piperidinediol, or (3S, 4S, 5S)-5-hydroxymethyl-1-methoxy-3,4-piperidinediol, or a pharmaceutically acceptable salt or tautomeric form thereof.

27. A compound of claim 1 which is:

1-(2-(4'-fluoroacetophenone))-5-hydroxymethyl-3,4-piperidinediol, hydroxymethyl-1-(2-(4'-methoxyacetophenone))-3,4-piperidinediol, 5-hydroxymethyl-1-(4-N,N-diphenylaminobenzyl)-3,4-piperidinediol, (3,4-dihydroxy-5-hydroxymethyl-piperidin-1-yl)-acetamide, 1-(2-(4'-fluoroacetophenone))-5-hydroxymethyl-3,4-piperidinediol, 5-hydroxymethyl-1-(2-(4'-methoxyacetophenone))-3,4-piperidinediol, 5-hydroxymethyl-1-(4-N,N-diphenylaminobenzyl)-3,4-piperidinediol, or (3,4-dihydroxy-5-hydroxymethyl-piperidin-1-yl)-acetamide, or a pharmaceutically acceptable salt, optical isomer or mixture of optical isomers, or tautomeric form thereof.

28. A compound of claim 27 which is:

(3R, 4R, 5R)-1-(2-(4'-fluoroacetophenone))-5-hydroxymethyl-3,4-piperidinediol, (3R, 4R, 5R)-5-hydroxymethyl-1-(2-(4'-methoxyacetophenone))-3,4-piperidinediol, (3R, 4R, 5R)-5-hydroxymethyl-1-(4-N,N-diphenylaminobenzyl)-3,4-piperidinediol, (3R, 4R, 5R)-(3,4-dihydroxy-5-hydroxymethyl-piperidin-1-yl)-acetamide, (3S, 4S, 5S)-1-(2-(4'-fluoroacetophenone))-5-hydroxymethyl-3,4-piperidinediol, (3S, 4S, 5S)-5-hydroxymethyl-1-(2-(4'-methoxyacetophenone))-3,4-piperidinediol, (3S, 4S, 5S)-5-hydroxymethyl-1-(4-N,N-diphenylaminobenzyl)-3,4-piperidinediol, or (3S, 4S, 5S)-(3,4-dihydroxy-5-hydroxymethyl-piperidin-1-yl)-acetamide, or a pharmaceutically acceptable salt or tautomeric form thereof.

29. A compound of claim 1 which is:

ethyl (3,4-dihydroxy-5-hydroxymethyl-piperidin-1-yl) acetate, 12-(3,4-dihydroxy-5-hydroxymethyl-piperidin-1-yl)-dodecanoic acid, or 3-(3,4-dihydroxy-5-hydroxymethyl-piperidin-1-yl) propionic acid, or a pharmaceutically acceptable salt, or optical isomer or mixture of optical isomers, or tautomeric form thereof.

30. A compound of claim 29 which is:
(3R, 4R, 5R)-ethyl (3,4-dihydroxy-5-hydroxymethyl-piperidin-1-yl)acetate,
(3R, 4R, 5R)-12-(3,4-dihydroxy-5-hydroxymethyl-piperidin-1-yl)-dodecanoic acid,
(3R, 4R, 5R)-3-(3,4-dihydroxy-5-hydroxymethyl-piperidin-1-yl)propionic acid,
(3S, 4S, 5S)-ethyl (3,4-dihydroxy-5-hydroxymethyl-piperidin-1-yl)acetate,
(3S, 4S, 5S)-12-(3,4-dihydroxy-5-hydroxymethyl-piperidin-1-yl)-dodecanoic acid, or
(3S, 4S, 5S)-3-(3,4-dihydroxy-5-hydroxymethyl-piperidin-1-yl)propionic acid,
or a pharmaceutically acceptable salt or tautomeric form thereof.

31. A pharmaceutical composition comprising a compound of claim 1 together with one or more pharmaceutically acceptable carriers or diluents.

32. The pharmaceutical composition of claim 31 in the form of an oral dosage unit or parenteral dosage unit.

33. A method of treating or preventing a disorder in a subject in need thereof comprising administering an effective amount of a compound of claim 1, wherein the disorder is diabetes, hyperglycemia, hypercholesterolemia, hypertension, hyperinsulinemia, hyperlipidemia, atherosclerosis or myocardial ischemia.

34. A method of treating or preventing non-insulin dependent diabetes mellitus in a subject in need thereof, comprising administering an effective amount of a compound of claim 1, and/or treating or preventing long-term complications, wherein the complication is retinopathy, neuropathy, nephropathy and micro- or macroangiopathy.

* * * * *

UNITED STATES PATENT AND TRADEMARK OFFICE
CERTIFICATE OF CORRECTION

PATENT NO. : 6,046,214
DATED : April 4, 2000
INVENTOR(S) : Kristiansen et al.

Page 1 of 1

It is certified that error appears in the above-identified patent and that said Letters Patent is hereby corrected as shown below:

Column 26,
Line 14, delete "R4", and insert -- $R_4$ --.

Signed and Sealed this

Second Day of October, 2001

Attest:

*Attesting Officer*

NICHOLAS P. GODICI
*Acting Director of the United States Patent and Trademark Office*